United States Patent
Nan et al.

(10) Patent No.: US 10,316,008 B2
(45) Date of Patent: Jun. 11, 2019

(54) KCNQ POTASSIUM CHANNEL AGONIST, AND PREPARATION METHOD THEREFOR AND USE THEREOF

(71) Applicant: SHANGHAI INSTITUTE OF MATERIA MEDICA, CHINESE ACADEMY OF SCIENCES, Shanghai (CN)

(72) Inventors: Fajun Nan, Shanghai (CN); Min Li, Shanghai (CN); Zhaobing Gao, Shanghai (CN); Yangming Zhang, Shanghai (CN); Haining Hu, Shanghai (CN); Haiyan Xu, Shanghai (CN); Huanan Liu, Shanghai (CN); Xiaoping Pi, Shanghai (CN)

(73) Assignee: SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 0 days.

(21) Appl. No.: 15/870,276

(22) Filed: Jan. 12, 2018

(65) Prior Publication Data
US 2018/0134677 A1    May 17, 2018

Related U.S. Application Data

(63) Continuation of application No. 15/306,971, filed as application No. PCT/CN2015/077216 on Apr. 22, 2015, now abandoned.

(30) Foreign Application Priority Data

Apr. 28, 2014  (CN) .......................... 2014 1 0175315

(51) Int. Cl.
| | | |
|---|---|---|
| *C07D 307/24* | (2006.01) |
| *A61K 31/167* | (2006.01) |
| *A61K 31/17* | (2006.01) |
| *A61K 31/27* | (2006.01) |
| *A61K 31/277* | (2006.01) |
| *A61K 31/341* | (2006.01) |
| *C07C 269/04* | (2006.01) |
| *C07C 269/06* | (2006.01) |
| *C07C 271/28* | (2006.01) |
| *C07C 273/18* | (2006.01) |

(Continued)

(52) U.S. Cl.
CPC .......... *C07D 307/24* (2013.01); *A61K 31/167* (2013.01); *A61K 31/17* (2013.01); *A61K 31/27* (2013.01); *A61K 31/277* (2013.01); *A61K 31/341* (2013.01); *C07C 231/02* (2013.01); *C07C 233/62* (2013.01); *C07C 235/16* (2013.01); *C07C 235/74* (2013.01); *C07C 237/04* (2013.01); *C07C 237/22* (2013.01); *C07C 237/48* (2013.01); *C07C 269/04* (2013.01); *C07C 269/06* (2013.01); *C07C 271/28* (2013.01); *C07C 273/18* (2013.01); *C07C 275/64* (2013.01); *C07C 333/08* (2013.01); *C07C 2601/02* (2017.05); *C07C 2601/14* (2017.05)

(58) Field of Classification Search
CPC .............................. C07D 307/24; A61K 31/167
See application file for complete search history.

(56) References Cited

U.S. PATENT DOCUMENTS

| | | |
|---|---|---|
| 5,384,330 A | 1/1995 | Dieter et al. |
| 5,852,053 A | 12/1998 | Rostock et al. |

(Continued)

FOREIGN PATENT DOCUMENTS

| | | |
|---|---|---|
| CN | 1761464 | 4/2006 |
| CN | 101056845 | 10/2007 |

(Continued)

OTHER PUBLICATIONS

Wulff, Heike, et al., "Voltage-Gated Potassium Channels as Therapeutic Targets," Nature Reviews, Drug Discovery, 2009, vol. 8, No. 12, pp. 982-1001.

(Continued)

*Primary Examiner* — Golam M Shameem
(74) *Attorney, Agent, or Firm* — Ping Wang; Morris, Manning & Martin, LLP

(57) ABSTRACT

The present invention provides a compound represented by general formula I or a pharmaceutical acceptable salt thereof, the preparation method therefor and the use thereof in preparing a medicine for treating a neurological disease, such as epilepsy, convulsion, neuropathic pain, acute ischemic stroke, and a neurodegenerative disease. The compound according to present invention has a better absorption in brain tissue when compared with RTG. In addition, the compound provided by present invention has not only a greatly enhanced efficacy, but also a neurotoxicity greatly lower than that of RTG, and thus possesses a wider safety window.

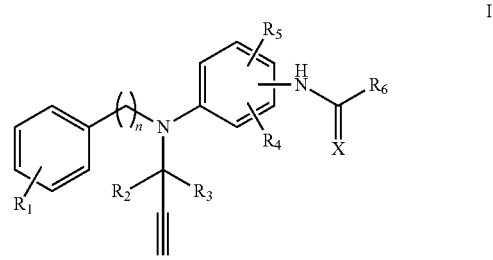

I

17 Claims, 2 Drawing Sheets

(51) Int. Cl.
  *C07C 275/64* (2006.01)
  *C07C 231/02* (2006.01)
  *C07C 333/08* (2006.01)
  *C07C 233/62* (2006.01)
  *C07C 235/16* (2006.01)
  *C07C 235/74* (2006.01)
  *C07C 237/04* (2006.01)
  *C07C 237/22* (2006.01)
  *C07C 237/48* (2006.01)

(56) References Cited

U.S. PATENT DOCUMENTS

| | | | |
|---|---|---|---|
| 7,906,537 | B2 | 3/2011 | Khanzhin et al. |
| 9,353,048 | B2 | 5/2016 | Nan et al. |

FOREIGN PATENT DOCUMENTS

| | | |
|---|---|---|
| CN | 10 307 3455 | 5/2013 |
| WO | 2009083526 | 7/2009 |
| WO | 2011/012659 | 2/2011 |
| WO | 2013/060097 | 5/2013 |

OTHER PUBLICATIONS

Brown, David A., et al., "Neural KCNQ (Kv7) Channels," British Journal of Pharmacology, Mar. 2009, vol. 156, pp. 1185-1195.
Wulff, Heike, et al., "K+ Channel Modulators for the Treatment of Neurological Disorders and Autoimmune Diseases," American Chemical Society, Chemical Reviews, 2008, vol. 108, No. 5, pp. 1744-1773.
Dalby-Brown, William, et al., "Kv7 Channels: Function, Pharmacology and Channel Modulators," Bentham Science Publishers Ltd., Current Topics in Medicinal Chemistry, 2006, vol. 6, No. 10, pp. 999-1023.
Rode, Frederik, et al., "Functional Effects of the KCNQ Modulators Retigabine and XE991 in the Rat Urinary Bladder," Elsevier B.V., European Journal of Pharmacology, 2010, vol. 638, pp. 121-127.
Yu, Frank H., et al., "The VGL-Chanome: A Protein Superfamily Specialized for Electrical Signaling and Ionic Homeostasis," Science's STKE, Science Signaling, 2004, vol. 253, pp. 1-17.
Jankovic, Slobodan, et al., "The Preclinical Discovery and Development of Ezogabine for the Treatment of Epilepsy," Expert Opinion on Drug Discovery, 2013, vol. 8, No. 11, pp. 1429-1437.
Nan et al (2013): STN International, HCAPLUS database (Columbus, Ohio), Accession No. 2013: 686414.
File History of U.S. Appl. No. 15/306,971, filed Oct. 26, 2016.

KCNQ POTASSIUM CHANNEL AGONIST, AND PREPARATION METHOD THEREFOR AND USE THEREOF

This application is a Continuation of U.S. application Ser. No. 15/306,971, filed Oct. 26, 2016, which claims priority to International Patent Application No. PCT/CN2015/077216, filed Apr. 22, 2015, which claims priority to Chinese Patent Application No. 201410175315.X, filed Apr. 28, 2014. The entirety of the aforementioned applications is incorporated herein by reference.

FIELD

The present invention belongs to pharmaceutical field, and in particular, relates to a novel KCNQ potassium channel agonist, the preparation therefor and the use of the KCNQ potassium channel agonist or the pharmaceutically acceptable salt thereof or a pharmaceutical composition comprising same in preparing a medicament for treating neurological diseases, such as epilepsy, convulsion, neuropathic pain acute ischemic stroke, and neurodegenerative diseases.

BACKGROUND

Ion channel is an important membrane protein family in cell membrane. It plays an important role in the process of neuromuscular excitement, hormone secretion, cell differentiation, sensory conduction, learning and memory, blood pressure control, salt and water balance, etc. It has been found through studies that mutations of more than 60 kinds of ion channels are closely related to disease. At present, ion channel has become the third-largest drug target following GPCR (G protein coupled receptor) and protein kinase (Yu et al., *Science's STKE*, 2004, 253, 15-21). There are more than 400 kinds of genes encoding ion channels in human genome, wherein the potassium ion channel superfamily has the most members. Potassium ion channels can be classified into four main categories according to their functions and structural features: inward rectifier potassium channels ($K_{ir}$), two pore potassium channel ($K_{2p}$), calcium-activated potassium channel ($K_{Ca}$) and voltage-gated potassium channel ($K_v$) (H. Wulff et al., *Nature Reviews Drug Discovery*, 2009, 8(12), 982-1001). Potassium ion channels play an important role in the regulation of excitability of neurons. The ion mechanism thereof is that the intracellular concentration of potassium ion is higher than the extracellular concentration, positively charged potassium ions efflux after the depolarization of membrane potential activates the channel, and thus membrane potential becomes negative (negative polarization or hyperpolarization) and cell excitability is decreased. Recent studies on epileptic genetics have shown that abnormalities of potassium ion channel can directly lead to epilepsy (H. Wulff et al., *Chemical Review*, 2008, 108(5), 1744-1773), such as benign neonatal familial convulsions (BFNC).

The voltage-gated potassium channel ($K_v$) is an important member of the potassium channel superfamily, and includes 12 members, $K_v1.X$ to $K_v12.X$. The KCNQ channel is the 7th member ($K_v7$) of the voltage-gated potassium channels, and includes 5 subtypes named KCNQ1 to KCNQ5, respectively. The locations and functions of different KCNQ subtypes are different, for example, KCNQ1 mainly locates in heart and cochlea, and its mutation is closely related to congenital long-qt syndrome and congenital deafness; KCNQ2, KCNQ3 and KCNQ5 mainly locate in brain and ganglia, and are closely related to neuronal excitability; and KCNQ4 mainly locates in cochlear and vestibular hair cells, and is closely related to audition (D. A. Brown, et al., *British Journal of Pharmacology*, 2009, 156, 1185-1195). Compared with other voltage-gated potassium channel members, KCNQ channel has a relatively low activation threshold, and can be opened at an action potential of −60 mV, and the activation of the KCNQ channel is relative slow, and the KCNQ channel does not loss the activity thereof even during a sustained depolarization. These features make the KCNQ channel at the fundamental level in regulating cell excitability, the opening of KCNQ channel can inhibit neural excitability, and the inhibition of the functions of KCNQ channel can lead to the depolarization of nervous cell membrane potential, and thus increasing excitability, and inducing more nerve impulses. Therefore, KCNQ channel is an important medical target for preventing and treating a variety of nerve excitatory disorders.

Based on the above features of KCNQ target, a KCNQ potassium channel agonist can be used for treating not only epilepsy, but also other disorders caused by excessive neural excitability, such as convulsion, neuropathic pain, acute ischemic stroke, and neurodegenerative diseases, by activating possium channels and decreasing neural excitability (Dalby-Brown et al., *Current Topics in Medicinal Chemistry*, 2006, 6, 999-1023).

The reported KCNQ potassium channel agonists are as follows:

1. U.S. Pat. No. 5,384,330 discloses some compounds having the following structure,

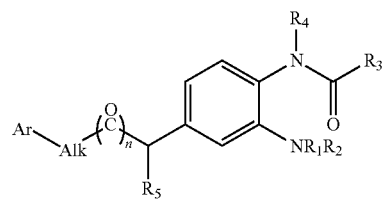

which are characterized by a benzene ring substituted by ortho-diamino groups.

2. WO2005/087754 discloses a KCNQ potassium channel agonist having the following structure,

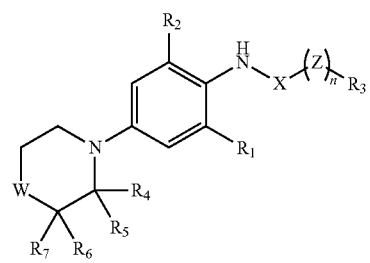

which is characterized by a benzene ring substituted by para-diamino groups, wherein one nitrogen is located in a saturated ring (or a heterocyclic ring when W is oxygen), and the adjacent positions of the other nitrogen are substituted by $R_1$ and $R_2$.

3. WO2008024398 describes the following structure,

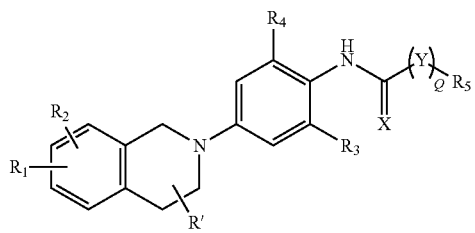

which has a similar structure as that described in WO2005/087754, with a fused benzene ring structural unit on the N-heterocyclic hydrocarbon.

Up to date, the most representative KCNQ potassium channel agonist is retigabine (hereafter referred as RTG), an anti-epileptic drug developed by GSK (GlaxoSmithKline)) and marketed in 2011, with the following structure. RTG, which is the first systematic studied KCNQ potassium channel agonist, can activate KCNQ2-5 and is mainly used for treating adult patients suffering from partial seizure of epilepsy.

The structure of RTG contains an electron-rich benzene ring substituted by three amino groups, which results in that RTG is particularly easy to be oxidized and deteriorated during synthesis and storage. At the same time, there are many adverse reactions in clinical application, including dizziness, drowsiness, fatigue, confusion, tremor, poor coordination, diplopia, blurred vision, attention deficit, hypomnesis, ataxia, aphasia, dysphonia, disequilibrium, increased appetite, hallucinations, myoclonus, peripheral edema, hypokinesia, dry mouth, dysphagia, etc. Paruria is also a common toxic and side effect of RTG, including bladder swelling, thick-walled bladder, uroschesis, etc. On Apr. 26, 2013, the Drug Safety Commission of FDA announced that some of the color reactions were caused by RTG in the clinical application, including blue discoloration of the skin, retinal pigment abnormalities, etc. Given the specific mechanism of action is not clear, the patients receiving RTG is advised to take eye exam regularly (S. Jankovic et al., *Expert Opinion on Drug Discovery*, 2013, 8(11), 1-9; F. Rode et al., *European Journal of Pharmacology*, 2010, 638, 121-127).

WO2013060097, which is an early stage outcome made by the inventors of present invention and incorporated herein by reference in its entirety, discloses a KCNQ potassium channel agonist having the following structure:

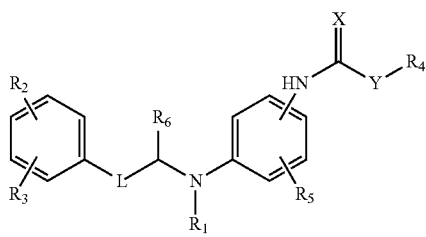

wherein, when $R_1$ is allyl or propargyl, the compound not only retains the activity of activating the KCNQ potassium ion channel equal to or higher than that of RTG, but also exhibits a significant anti-epileptic action in vivo, with a protective effect comparable to that of RTG. Furthermore, preliminary pharmacokinetic study in mice demonstrated that the compound has a higher exposure amount in brain tissue than RTG. However, further safety assessment revealed that the compounds disclosed in WO2013060097 have a high neurotoxicity, for example, death of rats can be observed when the dose is greater than 30 mg/kg in the case of single oral administration of compound K21. The lethal dose is obviously higher than the reported lethal dose of RTG (100 mg/kg, according to data from FDA Pharmacology Review(s), Potiga tablets).

SUMMARY

During studying the distribution of RTG in tissues, the inventors of the present invention have found that the distribution concentration in brain tissue is not high after administration of RTG. Specifically, the exposure amount of RTG in brain tissue of mice is only 14-16% of the exposure amount in plasma thereof after intravenous administration or oral administration (WO2013060097). The inventors of the present invention believe that low exposure amount of RTG in brain tissue not only affects maximum effectiveness thereof in the brain, but also may be one of important factors inducing adverse reactions of RTG. Meanwhile, RTG itself does not have a satisfied stability, and the inventors of the present invention found that the aqueous solution of RTG hydrochloride quickly become blue and insoluble precipitate is formed when the solution is exposed to air. The inventors of present invention believe that the instability of the drug itself may be associated with the color reaction observed in clinical application. In view of the above disadvantages of the existing KCNQ potassium ion channel agonist, it is necessary to develop a novel potassium ion channel agonist which has a more stable physical property, a higher activity, a lower toxicity, and a wide safety window, and facilitates the distribution in brain tissue, so as to be used in manufacturing a novel medicament for treating neurogenic diseases, such as epilepsy, convulsion, neuropathic pain, acute ischemic stroke etc., and neurodegenerative diseases, such as Alzheimer's disease, etc.

The inventors of the present invention have found in the preliminary work that the incorporated propargyl not only retains the KCNQ potassium channel agonistic activity of the RTG derivatives, but also, unexpectedly found in the pharmacokinetic study, greatly improves the distribution and exposure amount of the compound in brain tissue of the mice (WO2013060097), for example, the exposure amount of the compound K21 in brain tissue of mice is 2.4 time of that in plasma after the compound K21 is orally administered to mice. In the present invention, the present inventors have found through further researches that, on the basis of keeping the middle nitrogen atom substituted by propargyl, the compounds obtained by modifying k21 through removing the free amino group on the right benzene ring and introducing different substituents, especially alkyl, such as methyl, on the right benzene ring, not only have a stable physical property a with a absorption in brain tissue, but also have greatly enhanced activity of activating KCNQ potassium channel, for example, the agonistic activity of K43 on KCNQ2 homotetramer channel is more than 800 times of that of RTG, and the activity thereof on KCNQ2/3 heterotetramer channel is also better than those of the compound K21 disclosed in WO2013060097 and RTG. In addition, the present inventors found through further researches that, compared with RTG, the compounds according to present invention have not only improved activity in vivo and in vitro, but also significant reduced neurotoxicity, thus possess a wider therapeutic window. In summary, the novel compounds provided by present invention overcome many disadvantages of existing potassium channel agonists, and have a stable physical property, a excellent absorption in brain tissue, a greatly enhanced activity, a greatly reduced toxicity, a good oral absorption, and good pharmacokinetic parameters, and thus they have good development prospect.

One object of the present invention is to provide a novel compound which may be used as KCNQ potassium channel agonist.

Another object of the present invention is to provide a method for preparing the compound.

Yet another object of the present invention is to provide a pharmaceutical composition comprising the compound or a pharmaceutically acceptable salt thereof as an active ingredient and a pharmaceutically acceptable adjuvant.

Still another object of the present invention is to provide use of the compound, pharmaceutically acceptable salts thereof or the pharmaceutical composition containing same in preparing a medicament for treating a neurogenic disease etc.

In one aspect, the compound according to the present invention has the structure of following general formula I:

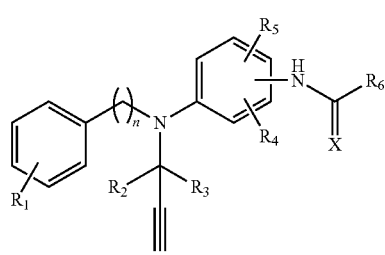

wherein,

X is oxygen or sulfur; n is 1, 2 or 3, preferably 1;

$R_1$ is H or halogen, preferably H or fluorine;

$R_2$ and $R_3$ are each independently selected from a group consisting of H, D and $C_1$-$C_3$ alkyl; or $R_2$ and $R_3$ together with the carbon atom to which they attached form $C_3$-$C_6$ saturated ring; preferably, $R_2$ and $R_3$ are each independently selected from a group consisting of H and D, or $R_2$ and $R_3$ together with the carbon atom to which they attached form cyclopropyl;

$R_4$ and $R_5$ are each independently selected from a group consisting of H; halogen; $C_1$-$C_6$ alkyl; $C_3$-$C_6$ cycloalkyl; cyano; $C_1$-$C_4$ alkoxyl; $C_1$-$C_6$ alkyl optionally substituted by hydroxy, amino, $C_1$-$C_4$ alkoxy, $C_1$-$C_4$ alkylcarbonyl, or halogen; $C_1$-$C_4$ alkoxy optionally substituted by halogen; $C_1$-$C_6$ alkylcarbonyl; $C_1$-$C_6$ alkoxycarbonyl; $C_1$-$C_6$ alkylaminocarbonyl; $C_2$-$C_6$ alkenyl; and $C_2$-$C_6$ alkynyl; preferably, $R_4$ and $R_5$ are each independently H, halogen, cyano, $C_1$-$C_4$ alkyl, $C_1$-$C_4$ alkoxy or $C_1$-$C_4$ fluoroalkoxy; more preferably, $R_4$ and $R_5$ are each independently H, halogen, $C_1$-$C_4$ alkyl or $C_1$-$C_4$ alkoxy; and most preferably, one of $R_4$ and $R_5$ is $C_1$-$C_4$ alkyl, and the other is H or $C_1$-$C_4$ alkyl;

$R_6$ is selected from a group consisting of $C_1$-$C_6$ alkoxy; $C_1$-$C_6$ alkylamino; $C_1$-$C_6$ alkyl; $C_3$-$C_6$ cycloalkyl; $C_2$-$C_6$ alkenyl; $C_2$-$C_6$ alkynyl; $C_6$-$C_{10}$ aryl; $C_1$-$C_6$ alkyl optionally substituted by halogen, cyano, hydroxy, $C_1$-$C_6$ alkoxyl, di($C_1$-$C_4$ alkyl)amino, $C_1$-$C_6$ alkylcarbonyl, $C_1$-$C_6$ alkylcarbonylamino, or $C_1$-$C_6$ alkoxycarbonyl; $C_3$-$C_6$ cycloalkyl optionally substituted by halogen; $C_2$-$C_6$ alkenyl optionally substituted by halogen; $C_2$-$C_6$ alkynyl optionally substituted by halogen; tetrahydrofuranyl; and

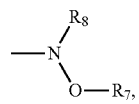

wherein, $R_7$ and $R_8$ are each independently selected from a group consisting of $C_1$-$C_4$ alkyl, provided that the above compound does not include

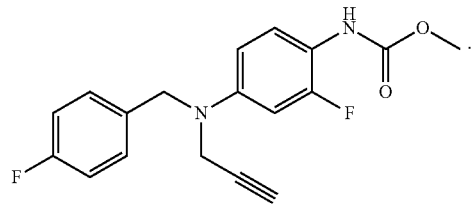

Further, the compound according to present invention may be the compound represented by the following general formula II:

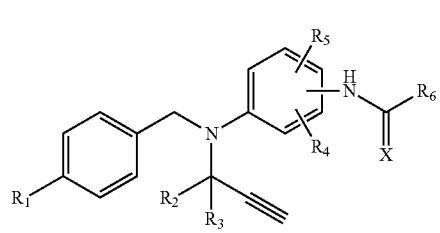

wherein,

X is oxygen or sulfur;

$R_1$ is H or halogen, preferably, $R_1$ is H or F;

$R_2$ and $R_3$ are each independently selected from a group consisting of H, D and $C_1$-$C_3$ alkyl; or $R_2$ and $R_3$ together with the carbon atom to which they attached form $C_3$-$C_6$ saturated ring; preferably, $R_2$ and $R_3$ are each independently selected from a group consisting of H and D, or $R_2$ and $R_3$ together with the carbon atom to which they attached form cyclopropyl;

$R_4$ and $R_5$ are each independently selected from a group consisting of H; halogen; $C_1$-$C_6$ alkyl; $C_3$-$C_6$ cycloalkyl; cyano; $C_1$-$C_4$ alkoxyl; $C_1$-$C_6$ alkyl optionally substituted by hydroxy, amino, $C_1$-$C_4$ alkoxy, $C_1$-$C_4$ alkylcarbonyl, or halogen; $C_1$-$C_4$ alkoxy optionally substituted by halogen; $C_1$-$C_6$ alkylcarbonyl; $C_1$-$C_6$ alkoxycarbonyl; $C_1$-$C_6$ alkylaminocarbonyl; $C_2$-$C_6$ alkenyl; and $C_2$-$C_6$ alkynyl; preferably, $R_4$ and $R_5$ are each independently H, halogen, cyano, $C_1$-$C_4$ alkyl, $C_1$-$C_4$ alkoxy or $C_1$-$C_4$ alkoxy; more preferably, $R_4$ and $R_5$ are each independently H, halogen, $C_1$-$C_4$ alkyl or $C_1$-$C_4$ alkoxy; and most preferably, one of $R_4$ and $R_5$ is $C_1$-$C_4$ alkyl, and the other is H or $C_1$-$C_4$ alkyl;

$R_6$ is selected from a group consisting of $C_1$-$C_6$ alkoxy; $C_1$-$C_6$ alkylamino; $C_1$-$C_6$ alkyl; $C_3$-$C_6$ cycloalkyl; $C_2$-$C_6$ alkenyl; $C_2$-$C_6$ alkynyl; $C_6$-$C_{10}$ aryl; $C_1$-$C_6$ alkyl optionally substituted by halogen, cyano, hydroxy, $C_1$-$C_6$ alkoxyl, di($C_1$-$C_4$ alkyl) amino, $C_1$-$C_6$ alkylcarbonyl, $C_1$-$C_6$ alkylcarbonylamino, or $C_1$-$C_6$ alkoxycarbonyl; $C_3$-$C_6$ cycloalkyl optionally substituted by halogen; $C_2$-$C_6$ alkenyl optionally substituted by halogen; $C_2$-$C_6$ alkynyl optionally substituted by halogen; tetrahydrofuranyl; and

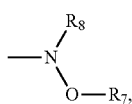

wherein, $R_7$ and $R_8$ are each independently selected from a group consisting of $C_1$-$C_4$ alkyl, provided that the above compound does not include

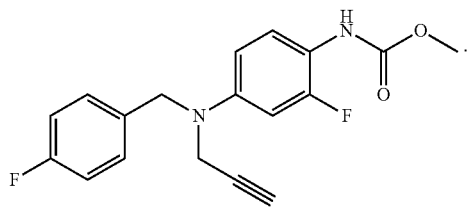 [SMILES: C#CCN(Cc1ccc(F)cc1)c1ccc(NC(=O)OC)c(F)c1]

Further, the compound according to present invention is selected from a group consisting of the compounds represented by the following general formula III to V:

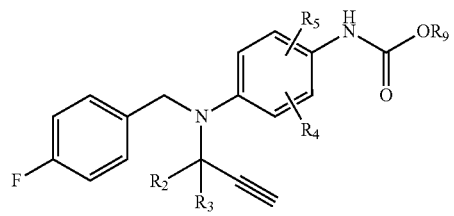

III

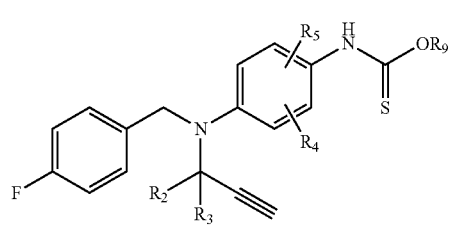

IV

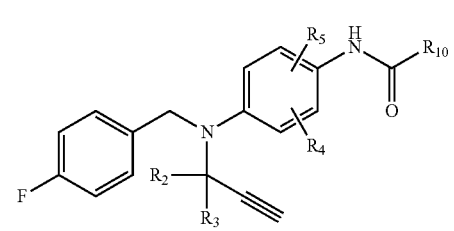

V wherein, $R_2$ and $R_3$ are each independently selected from a group consisting of H, D and $C_1$-$C_3$ alkyl; or $R_2$ and $R_3$ together with the carbon atom to which they attached form $C_3$-$C_6$ saturated ring; preferably, $R_2$ and $R_3$ are each independently selected from a group consisting of H and D, or $R_2$ and $R_3$ together with the carbon atom to which they attached form cyclopropyl;

$R_4$ and $R_5$ are each independently selected from a group consisting of H; halogen; $C_1$-$C_6$ alkyl; $C_3$-$C_6$ cycloalkyl; cyano; $C_1$-$C_4$ alkoxy; $C_1$-$C_6$ alkyl optionally substituted by hydroxy, amino, $C_1$-$C_4$ alkoxy, $C_1$-$C_4$ alkoxycarbonyl, or halogen; $C_1$-$C_4$ alkoxy optionally substituted by halogen; $C_1$-$C_6$ alkylcarbonyl; $C_1$-$C_6$ alkoxycarbonyl; $C_1$-$C_6$ alkylaminocarbonyl; $C_2$-$C_6$ alkenyl; and $C_2$-$C_6$ alkynyl; further preferably, $R_4$ and $R_5$ are each independently H, $C_1$-$C_6$ alkyl, or $C_1$-$C_4$ alkoxyl; more preferably, $R_4$ and $R_5$ are each independently H, halogen, cyano, $C_1$-$C_4$ alkyl or $C_1$-$C_4$ alkoxy; further more preferably, $R_4$ and $R_5$ are each independently H, halogen, $C_1$-$C_4$ alkyl or $C_1$-$C_4$ alkoxy; and most preferably, one of $R_4$ and $R_5$ is $C_1$-$C_4$ alkyl, and the other is H or $C_1$-$C_4$ alkyl;

$R_9$ is selected from a group consisting of $C_1$-$C_6$ alkyl and $C_3$-$C_6$ cycloalkyl; preferably, $R_9$ is selected from a group consisting of methyl, ethyl and propyl;

$R_{10}$ is selected from a group consisting of $C_1$-$C_6$ alkyl; $C_1$-$C_6$ alkyl optionally substituted by halogen, cyano, hydroxy, $C_1$-$C_6$ alkoxyl, di($C_1$-$C_4$ alkyl)amino, $C_1$-$C_6$ alkylcarbonyl, $C_1$-$C_6$ alkylamido, or $C_1$-$C_6$ alkoxycarbonyl; $C_3$-$C_6$ cycloalkyl optionally substituted by halogen; tetrahydrofuranyl; and

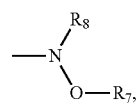

wherein, $R_7$ and $R_8$ are each independently selected from a group consisting of $C_1$-$C_4$ alkyl; preferably, $R_{10}$ is selected from a group consisting of $C_1$-$C_3$ alkyl optionally substituted by halogen, cyano, hydroxy, $C_1$-$C_3$ alkoxyl, di($C_1$-$C_3$ alkyl) amino, $C_1$-$C_3$ alkylcarbonyl, $C_1$-$C_3$ alkylamido, $C_1$-$C_3$ alkoxycarbonyl; $C_3$-$C_6$ cycloakyl optionally substituted by halogen; tetrahydrofuranyl; and

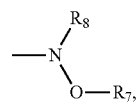

wherein, $R_7$ and $R_8$ are each independently selected from a group consisting of $C_1$-$C_3$ alkyl;

provided that the above compound does not include

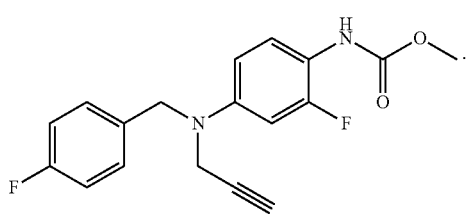 [SMILES: C#CCN(Cc1ccc(F)cc1)c1ccc(NC(=O)OC)c(F)c1]

In the compounds represented by above general formulae I to V, preferably, one of $R_4$ and $R_5$ is methyl, and the other is H or methyl.

According to the most preferable embodiments, parts of the representative compounds are listed as follows:

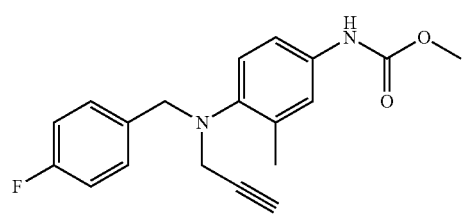 [SMILES: C#CCN(Cc1ccc(F)cc1)c1ccc(NC(=O)OC)cc1C] K40
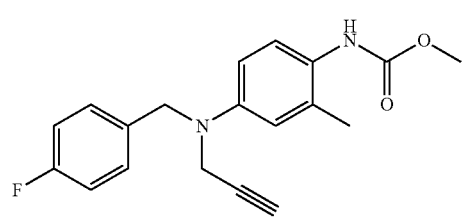 [SMILES: C#CCN(Cc1ccc(F)cc1)c1ccc(NC(=O)OC)c(C)c1] K41
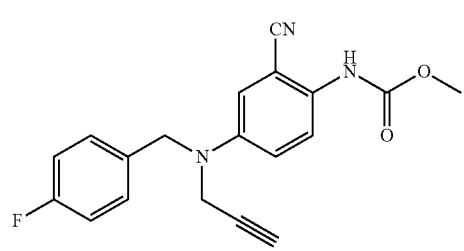 [SMILES: C#CCN(Cc1ccc(F)cc1)c1ccc(NC(=O)OC)c(C#N)c1] K42
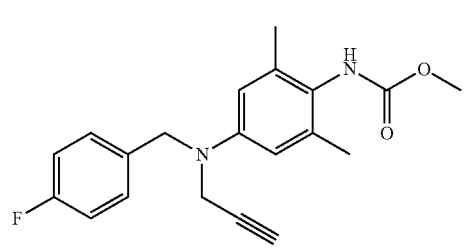 K43
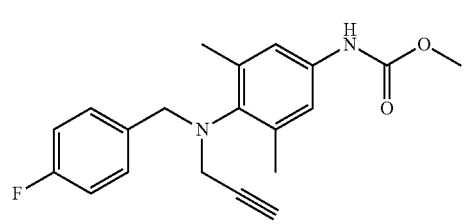 [SMILES: C#CCN(Cc1ccc(F)cc1)c1c(C)cc(NC(=O)OC)cc1C] K44
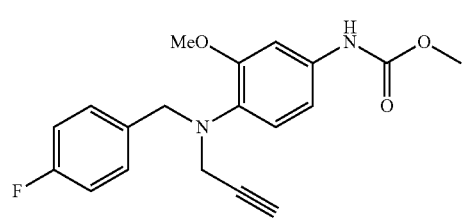 [SMILES: C#CCN(Cc1ccc(F)cc1)c1ccc(NC(=O)OC)cc1OC] K45
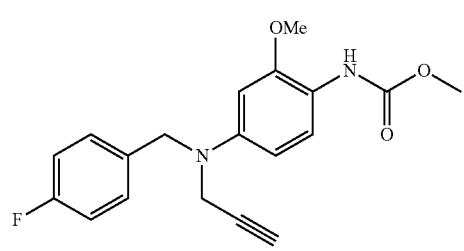 [SMILES: C#CCN(Cc1ccc(F)cc1)c1ccc(NC(=O)OC)c(OC)c1] K46
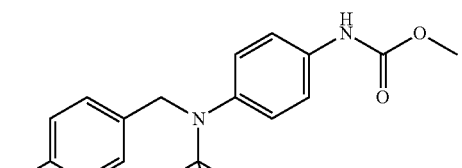 K47
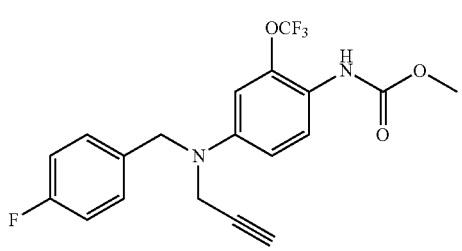 [SMILES: C#CCN(Cc1ccc(F)cc1)c1ccc(NC(=O)OC)c(OC(F)(F)F)c1] K48
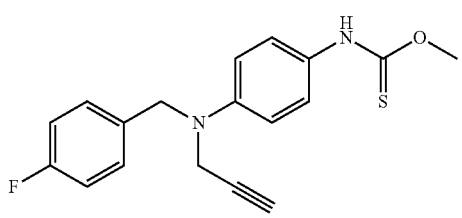 [SMILES: C#CCN(Cc1ccc(F)cc1)c1ccc(NC(=S)OC)cc1] K49
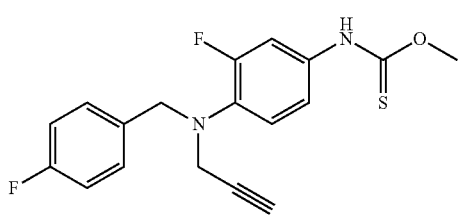 K50
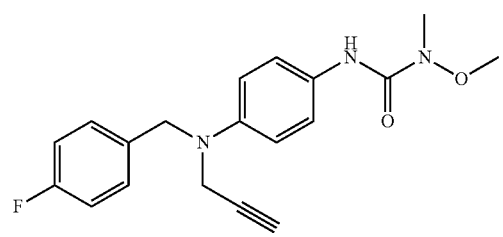 K51
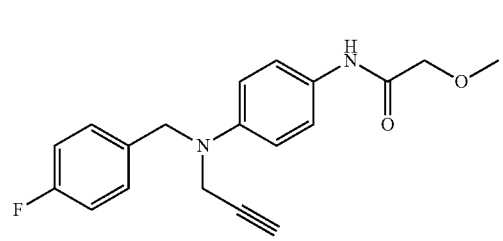 K52
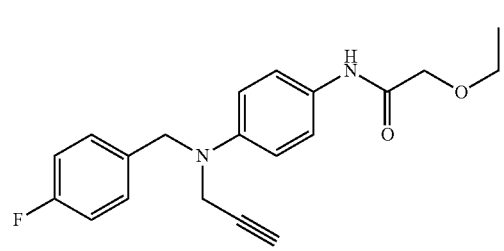 K53

-continued

K54
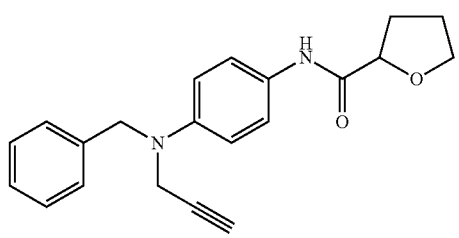

K55
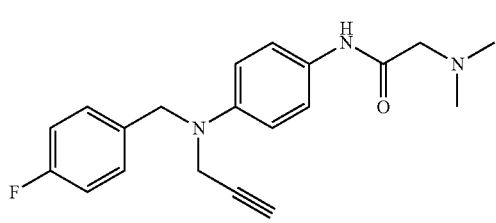

K56
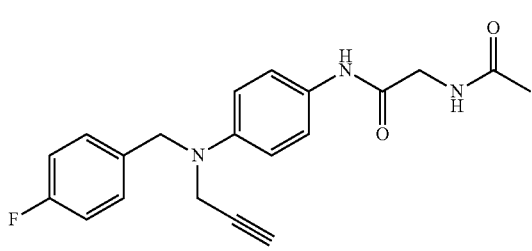

K57
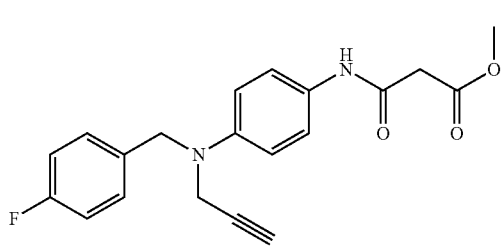

K58
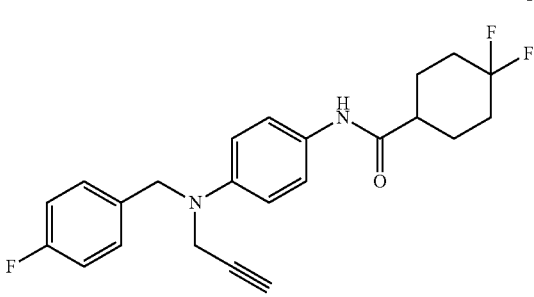

K59
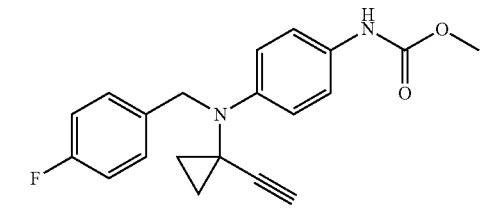

The pharmaceutically acceptable salt of the compound according to the present invention may be a salt formed by the above compound with an acid, and the acid is selected from the group consisting of maleic acid, succinic acid, citric acid, tartaric acid, fumaric acid, formic acid, acetic acid, propanoic acid, propandioic acid, oxalic acid, benzoic acid, phthalic acid, methanesulfonic acid, benzenesulfonic acid, toluenesulfonic acid, naphthalenesulfonic acid, 1,5-naphthalenedisulfonic acid, camphoric acid, camphor sulfonic acid, salicylic acid, acetyl salicylic acid, aspartic acid, glutamic acid, lactic acid, gluconic acid, ascorbic acid, gallic acid, amygdalic acid, malic acid, sorbic acid, trifluoroacetic acid, taurine, homotaurine, isethionic acid, cinnamic acid, hydrochloric acid, hydrobromic acid, hydroiodic acid, sulfuric acid, nitric acid, phosphoric acid and perchloric acid.

In another aspect of the present invention, provided is a method for preparing the compound or pharmaceutically acceptable salts thereof according to present invention, the method may be one of the following.

Method I

Aldehyde a reacts with substituted aniline b through reductive amination to give a secondary amine c. The secondary amine c reacts with propargyl bromide through substitution to give an intermediate d. The intermediate d is deprotected off the amino-protecting group P to give an intermediate, amine e, which is further reacted to give the compound represented by general formula I:

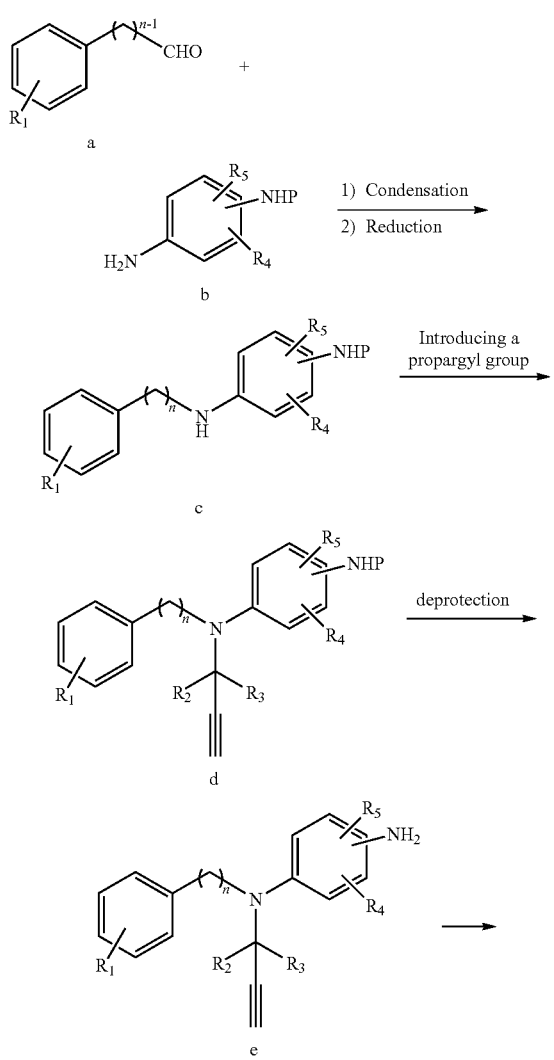

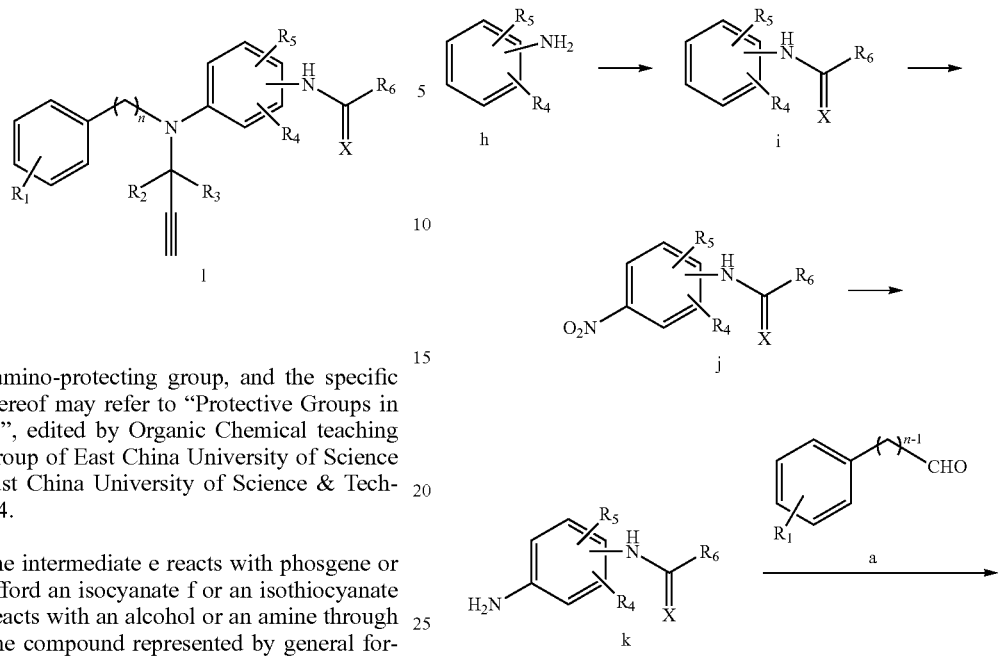

wherein P is an amino-protecting group, and the specific selection scope thereof may refer to "Protective Groups in Organic Synthesis", edited by Organic Chemical teaching and researching group of East China University of Science & Technology, East China University of Science & Technology press, 2004.

Method II

Alternatively, the intermediate e reacts with phosgene or thiophosgene to afford an isocyanate f or an isothiocyanate g, which further reacts with an alcohol or an amine through addition to give the compound represented by general formula I:

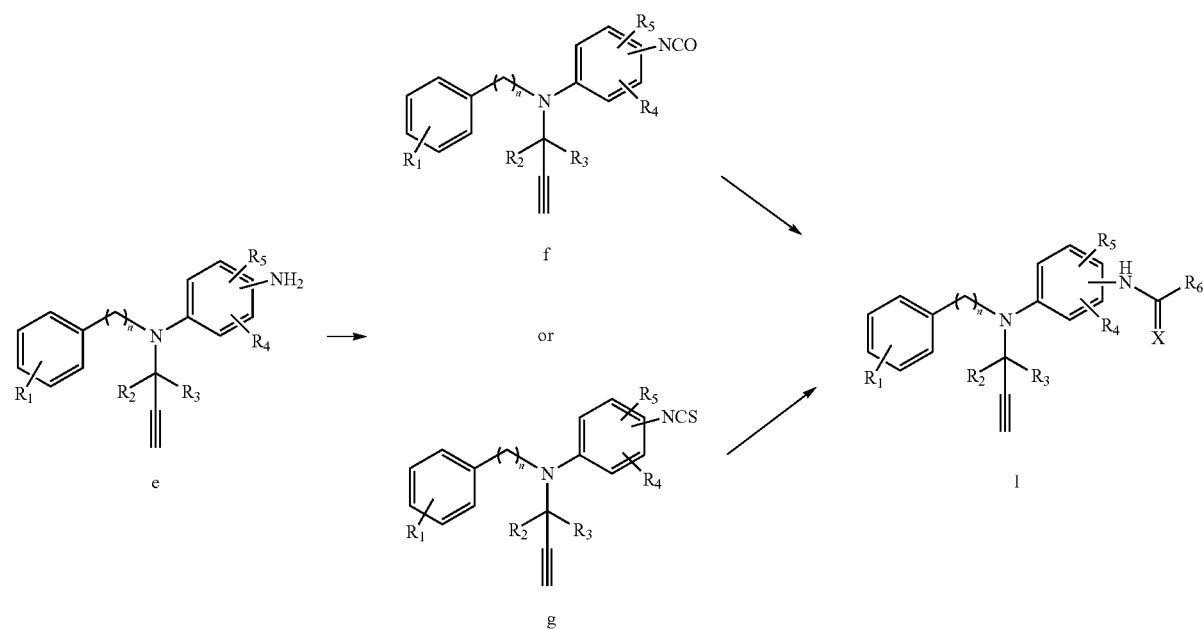

Method III

Alternatively, arylamine h is directly derived to give an intermediate i, which undergoes a nitration reaction to introduce a nitro group to give a nitro-compound j. The latter is further reduced to give an amine k, which reacts with an aldehyde a through a reductive amination to give an intermediate, secondary amine m. The secondary amine m reacts with propargylbromide through substitution to give the compound represented by general formula I:

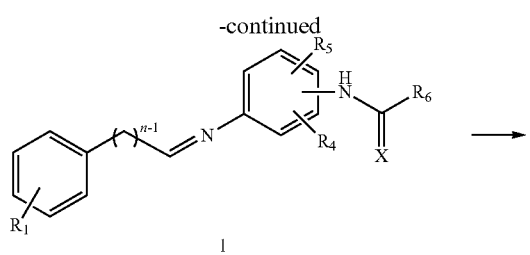

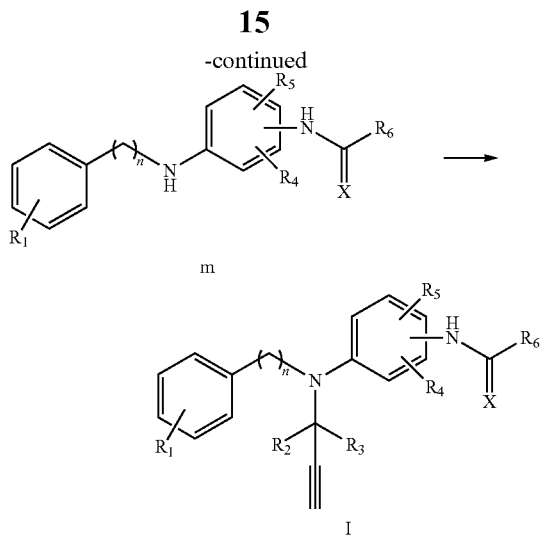

I

Method IV: Preparation for a Salt of the Compound

The compound of general formula I according to the present invention can be converted into a pharmaceutically acceptable salt thereof, such as hydrochloride. In general, the salt of the compound of present invention may be obtained by adding an acid solution into a solution of the compound, and after the salification is complete, removing the solvent under reduced pressure or filtering.

In the preparation method according to present invention, P is a protective group, and X, n, $R_1$, $R_2$, $R_3$, $R_4$, $R_5$, and $R_6$ are defined the same as above.

In another aspect of the present invention, provided is a pharmaceutical composition comprising the compound or the pharmaceutically acceptable salt thereof according to present invention as an active ingredient and a pharmaceutically acceptable adjuvant.

In yet another aspect of the present invention, provided is use of the compound and pharmaceutically acceptable salts thereof according to present invention or the pharmaceutical composition according to present invention as a KCNQ potassium channel agonist.

In still another aspect of present invention, provided is use of the compound and the pharmaceutically acceptable salt thereof according to present invention, or pharmaceutical composition containing any one of them in preparing a medicament for treating a neurological disease In yet another aspect of present invention, provided is a method for treating a neurological disease comprising administering to a subject suffering from a neurological disease the compound or the pharmaceutically acceptable salt thereof according to present invention or the pharmaceutical composition according to present invention.

The neurological disease includes epilepsy, convulsion, neuropathic pain, acute ischemic stroke, etc., and neurodegenerative diseases such as Alzheimer's disease etc.

Advantageous Effect

Compared with the existing drug RTG, since there is no free amino in the structure, the compound provided in the present invention are more stable in physical property and will not be readily oxidized and deteriorated, which is embodied in that the solution of such compound is not readily oxidized or discolored even exposed in air.

Compared with RTG, the compound provided in present invention has a better absorption in brain tissue. For example, when the compound K43 is orally administered to mice at a dose of 5 mg/kg, the exposure amount thereof in brain tissue is 7 times or more than that in plasma. As for rat, when the compound K43 is orally administered at a dose of 5 mg/kg, the exposure amount thereof in brain tissue is 3.9 times or more than that in plasma.

Compared with the existing KCNQ agonist, the compound provided in present invention has a greatly improved efficacy. For example, in an in vitro physiological experiment, the agonist activity of K43 on KCNQ2 homotetramer channel is more than 800 times of that of RTG, and the agonist activity of K43 on KCNQ2/3 heterotetramer channel is also significantly higher than those of the compound K21 disclosed in WO2013060097 and RTG. In addition, in in vivo pharmacodynamic mode for the efficacy, K43 and k41 also have an efficacy against MES (maximum electric shock) superior to that of RTG.

More importantly, the compound provided by present invention has not only a greatly enhanced efficacy, but also a greatly reduced neurotoxicity than RTG, and thus has a wide therapeutic window.

In summary, the compound provided by present invention overcome many disadvantages of the existing agonist, and has a stable physical property, a high activity, an excellent absorption in brain tissue, and a greatly reduced toxicity, and thus has a wider therapeutic window and a better therapeutic effect, showing a good application prospect.

DETAILED DESCRIPTION OF THE INVENTION

Figure 1:
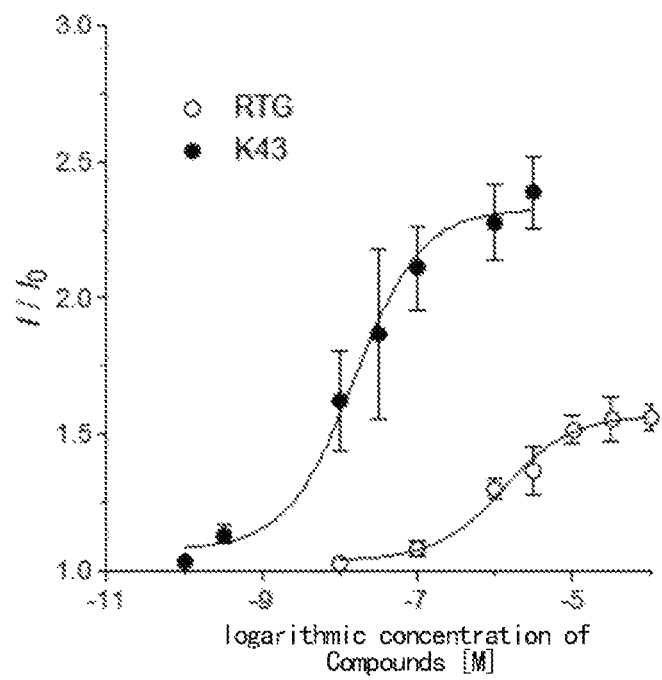
FIG. 1 is a graph showing the dose-response curves of K43 according to present invention and RTG on KCNQ2 homotetramer channel.

The present invention will be further illustrated based on the following examples, but the present invention will not be limited thereto.

I. Preparation Examples for Compounds

In following preparation examples, NMR was conducted on a Mercury-Vx 300M instrument manufactured by Varian with calibration of δH 7.26 ppm (CDCl$_3$), 2.50 ppm (DMSO-d6) and 3.15 ppm (CD3OD). The reagents were mainly provided by Shanghai Chemical Reagent Co. Ltd., and the silica gel plate (model HSGF 254) for thin layer chromatography (TLC) was manufactured by Huiyou Silica gel Development Co. Ltd., Yantai, Shandong. The compounds were purified by normal phase column chromatography with a silica gel (model zcx-11) of 200-300 mesh, manufactured by Branch of Qingdao Haiyang Chemical Co. Ltd.

Preparation Example 1

Preparation Example 1.1 Synthesis of methyl 4-(N-parafluorobenzyl-N-propargyl-amino)-2,6-dimethyl-phenylaminoformate (K43)

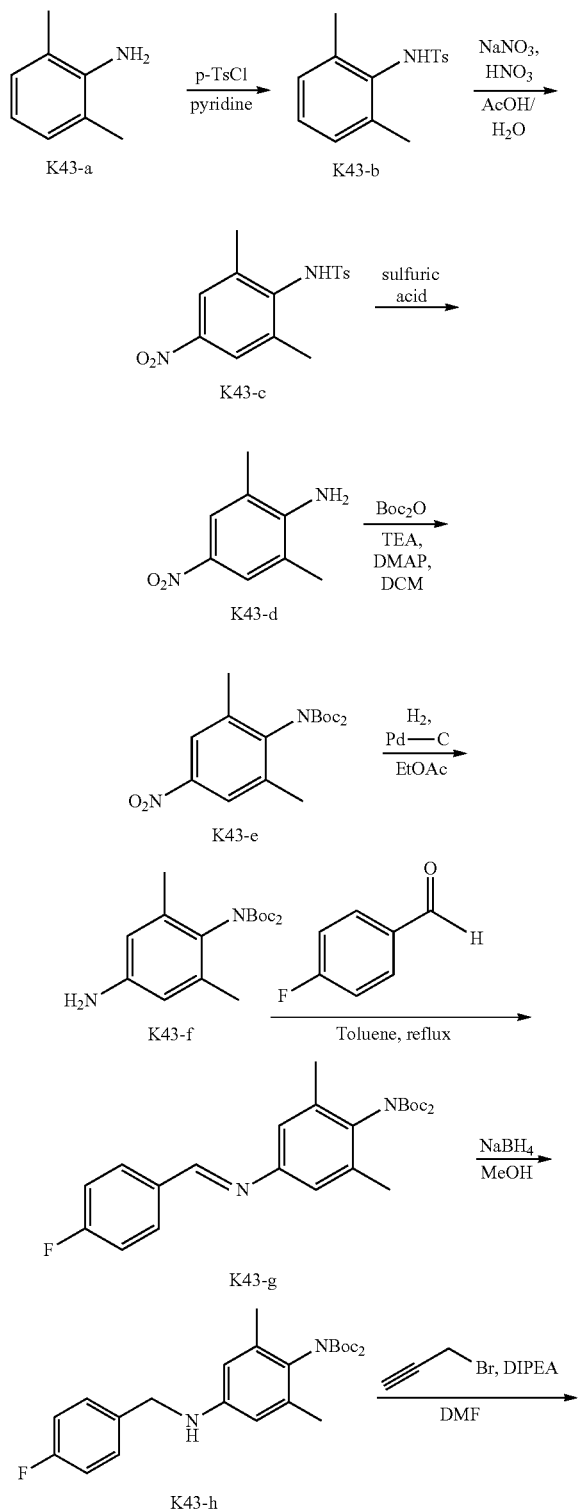

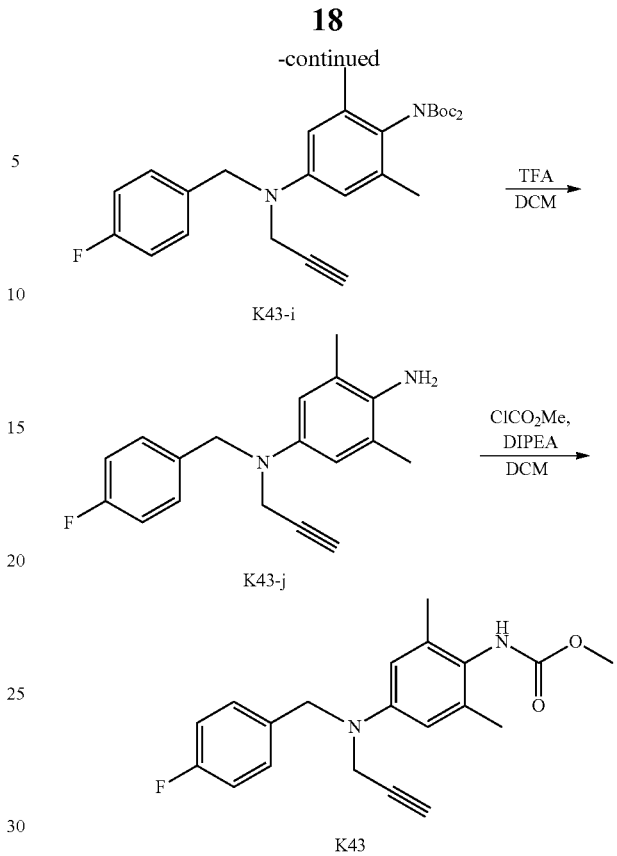

2,6-dimethylaniline K43-a (1.2 g, 10 mmol) was dissolved in dichloromethane (4 mL) and pyridine (25 mL), p-toluenesulfonyl chloride (p-TsCl) (2.29 g, 12 mmol) was added thereto and the obtained mixture was refluxed for 6 h. After cooled to room temperature, the reaction system was poured into a 3M HCl solution (20 mL), and then dichloromethane (20 mL) was added thereto. The organic phase obtained by phase separation was washed with water (20 mL) twice, and then concentrated. The residue was recrystallized in ethanol to give K43-b as a white solid (2.1 g, yield: 76%). $^1$H NMR (300 MHz, CDCl$_3$): δ 7.58 (d, J=8.4 Hz, 2H), 7.25 (d, J=8.4 Hz, 2H), 7.00-7.11 (m, 3H), 5.96 (s, 1H), 2.42 (s, 3H), 2.04 (s, 6H).

The obtained K43-b (2.10 g, 7.6 mmol) was dissolved in glacial acetic acid (AcOH) (40 mL), and then water (40 mL) and sodium nitrate (1.3 g, 15.2 mmol) were added thereto. The mixture was cooled to 0° C. by ice bath, and concentrated nitric acid was added thereto, and then the reaction mixture was heated to reflux for 4 h. After the completion of reaction was monitored by TLC, water (20 mL) was added and the mixture was cooled to 0° C. A large amount of yellowish solid was precipitated, and suction-filtered to give K43-c (19.g, yield: 78%), which was directly used in the next step.

K43-c (1.9 g, 5.9 mmol) and water (0.75 mL) were added into a round-bottomed flask, concentrated sulfuric acid (10 mL) was added thereto, and the mixture was kept under 40° C. overnight. The mixture was cooled to room temperature, and crushed ice and 2M aqueous sodium hydroxide solution (15 mL) were poured thereto. The mixture was extracted with ethyl acetate (50 mL), and the organic phase obtained was washed with water (20 mL) twice, and then with saturated saline (20 mL) once, dried with anhydrous sodium sulfate and concentrated to give K43-d as a yellow sold (980 mg, yield: 100%), which was directly used in the next step.

K43-d (1.52 g, 5.9 mmol) and dichloromethane (DCM) (40 mL) were added into a flask and dissolved under stirring. After the mixture was cooled to 0° C. by ice-water bath, di-t-butyl dicarbonate (Boc$_2$O) was added thereto (2.58 g, 11.8 mmol). Triethylamine (TEA) (1.77 mL, 12.9 mmol) and 4-Dimethylaminopyridine (DMAP) (722 mg, 5.9 mmol) were added under slowly stirring. After half an hour, the temperature was rise to room temperature and the reaction continued overnight. The reaction mixture was washed with 1M HCl (30 mL) once, and with water (50 mL) twice, and dried with anhydrous sodium sulfate. The crude product obtained by concentration was purified with silica gel column chromatography (petroleum ether/ethyl acetate=6:1) to give K43-e as a yellowish solid (1.84 g, yield: 85%), which was directly used in the next step.

K43-e (1.84 g, 5.0 mmol) obtained above was dissolved in ethyl acetate (EtOAc, 20 mL), 10% Pd/C (55 mg, 0.5 mmol) was added under nitrogen atmosphere. Hydrogen was purged three times and the reaction was performed under stirring at room temperature for 4 h. Hydrogen was removed, and nitrogen was purged three times. The reaction mixture was filtered, and the filtrate was concentrated to give K43-f (quantitative yield). $^1$H NMR (300 MHz, CDCl$_3$): δ 6.38 (s, 1H), 3.52 (s, 2H), 2.05 (s, 6H), 1.39 (s, 18H).

K43-f (366 mg, 1.0 mmol) obtained above and p-fluorobenzaldehyde (108 μL, 1.0 mmol) were added into a three-necked flask, toluene (10 mL) was added thereto, and after a water segregator was equipped onto the three-necked flask, the mixture was heated to reflux for 3 hour. The mixture was cooled to room temperature, and toluene was removed by vacuum concentration. The obtained crude K43-g was re-dissolved in methanol (20 mL), and sodium borohydride (NaBH$_4$) (76 mg, 2.0 mmol) was added thereto in batch under vigorous stirring. After the addition, the mixture continued to react for 2 h at room temperature. Crushed ice was added to quench the reaction, and then most of methanol was removed by vacuum concentration. The residue was dissolved in ethyl acetate (20 mL), washed with water (15 mL) twice and with saturated saline (10 mL) once, dried with anhydrous sodium sulfate. After concentration, the crude product was purified by silica gel column chromatography (petroleum ether/ethyl acetate=10:1) to give a benzyl substituted product K43-h (320 mg, yield: 72%; yellow solid).

K43-h (320 mg, 0.72 mmol) obtained above was dissolved in N,N-dimethylformamide (DMF, 5 ml), N,N-diisopropylethylamine (DIPEA) (257 μL, 1.44 mmol) and propargyl bromide (84 μL, 1.08 mmol) were added thereto. The reaction system was reacted at 65° C. for 4 h. Then, ethyl acetate (50 mL) was dropwisely added thereto. The resultant was washed with water (25 mL) twice, and then with saturated saline (20 mL) once, and then dried with anhydrous sodium sulfate. The residue was purified with silica gel column chromatography (petroleum ether/ethyl acetate=15:1) to give a propargyl-substituted intermediate K43-i (312 mg, yield 90%).

The intermediate K43-i (48 mg, 0.1 mmol) was dissolved in dichloromethane, and trifluoroacetic acid was added thereto under ice bath, and the temperature was kept for 2 h. After vacuum concentration, the resultant crude K43-i was redissolved in dichloroethane (1 mL), and DIPEA (35.0 μL, 0.2 mmol) and methyl chloroformate (11.7 μL, 0.15 mmol) were added thereto under ice-water bath. After the ice-water bath was removed, the reaction was kept at room temperature for 1 h. After concentration, the residue was purified with silica gel column chromatography (petroleum ether/ethyl acetate=8:1) to give K43 (31 mg, yield 92%). $^1$H NMR (300 MHz, CDCl$_3$): M 7.27 (dd, J=8.4, 5.4 Hz, 2H), 7.02 (t, J=9.0 Hz, 2H), 6.59 (s, 2H), 5.87 (brs, 1H), 4.48 (s, 2H), 3.96 (d, J=2.1 Hz, 2H), 3.73 (brs, 3H), 2.13 (s, 6H), 2.26 (t, J=2.1 Hz, 1H). $^{13}$C NMR (75 MHz, CDCl$_3$): R 163.6 (J=248.4 Hz), 155.2, 138.3, 137.5, 135.2, 133.7 (J=9.2 Hz), 125.2, 122.0, 116.1 (J=22.4 Hz), 80.4, 73.0, 58.7, 53.0, 47.0, 21.0. HR-ESIMS (m/z): calculated for $C_{20}H_{22}FN_2O_2$ [M+H]$^+$: 341.1665, found: 341.1656.

Preparation Example 1.2 The Following Compounds were Prepared in a Similar Manner as that in Preparation Example 1

| Compound | Formula | $^1$H NMR(CDCl$_3$, 300 MHz) data, δ |
|---|---|---|
| K40 | | 7.35 (dd, J$_1$ = 8.4 Hz, J$_2$ = 5.7 Hz, 2H), 7.17-7.26 (m, 3H), 6.97-7.03 (m, 2H), 6.75 (s, 1H), 4.15 (s, 2H), 3.76 (s, 3H), 3.56 (d, J = 2.1 Hz, 2H), 2.33 (s, 3H), 2.25 (t, J = 2.1 Hz, 1H). |
| K41 | | 7.41 (brs, 1H), 7.26-7.31 (m, 2H), 6.99-7.05 (m, 2H), 6.73-6.76 (m, 2H), 6.23 (s, 1H), 4.46 (s, 2H), 3.96 (d, J = 2.1 Hz, 2H), 3.75 (s, 3H), 2.22-2.24 (m, 4H). |

-continued

| Compound | Formula | $^1$H NMR(CDCl$_3$, 300 MHz) data, δ |
|---|---|---|
| K42 | | 7.88 (d, J = 8.7 Hz, 1H), 7.27-7.34 (m, 2H), 6.98-7.17 (m, 4H), 6.93 (s, 1H), 4.46 (s, 2H), 3.97 (d, J = 2.1 Hz, 2H), 3.78 (s, 3H), 2.27 (t, J = 2.1 Hz, 1H). |
| K44 | | 8.10 (d, J = 8.4 Hz, 1H), 7.86 (s, 1H), 7.35 (dd, J$_1$ = 1.2 Hz, J$_2$ = 8.4 Hz, 1H), 7.28 (ddd, J$_1$ = 3.0 Hz, J$_2$ = 4.8 Hz, J = 8.1 Hz, 2H), 7.18 (dd, J$_1$ = 1.2 Hz, J$_2$ = 7.8 Hz, 1H), 7.00 (ddd, J$_1$ = 2.7 Hz, J$_2$ = 3.9 Hz, J$_3$ = 11.4 Hz, 2H), 4.11 (s, 2H), 3.79 (s, 3H), 3.56 (d, J = 2.7 Hz, 2H), 2.27 (t, J = 2.4 Hz, 1H). |
| K45 | | 7.37 (dd, J$_1$ = 6.0 Hz, J$_2$ = 8.7 Hz, 2H), 7.24 (brs, 1H), 7.04 (d, J = 8.7 Hz, 1H), 6.98 (t, J = 8.7 Hz, 2H), 6.69 (dd, J$_1$ = 2.4 Hz, J$_2$ = 8.4 Hz, 1H), 6.63 (brs, 1H), 4.22 (s, 2H), 3.88 (s, 2H), 3.76 (s, 3H), 2.24 (t, J = 2.1 Hz, 1H). |
| K46 | | 7.89 (brs, 1H), 7.31 (dd, J$_1$ = 6.0 Hz, J$_2$ = 8.1 Hz, 2H), 6.94-7.05 (m, 3H), 6.53 (dd, J$_1$ = 2.4 Hz, J$_2$ = 9.0 Hz, 1H), 6.47 (s, 1H), 4.45 (s, 2H), 3.95 (d, J = 2.1 Hz, 2H), 3.79 (s, 3H), 3.72 (s, 3H), 2.58 (t, J = 2.1 Hz, 1H). |
| K48 | | δ 7.92 (brs, 1H), 7.25-7.30 (m, 2H), 7.03 (d, J = 8.7 Hz, 2H), 6.81 (dd, J = 8.7, 2.7 Hz, 1H), 6.77 (s, 1H), 6.63 (s, 1H), 4.46 (s, 2H), 3.96 (d, J = 2.1 Hz, 2H), 3.78 (s, 3H), 2.26 (t, J = 2.1 Hz, 1H). |
| K49 | | 8.40 (brs, 1H), 7.24 (dd, J = 8.4, 5.4 Hz, 2H), 7.11 (d, J = 9.3 Hz, 2H), 7.02 (d, J = 9.3 Hz, 2H), 6.82-6.85 (m, 2H), 4.50 (s, 2H), 4.10 (s, 3H), 3.93 (d, J = 2.1 Hz, 2H), 2.24 (t, J = 2.1 Hz, 1H). |

23

Preparation Example 2: Synthesis of methyl 4-(N-parafluorobenzyl-N-propargyl-amino)-2,6-dimethyl-phenylaminoformate (K43)

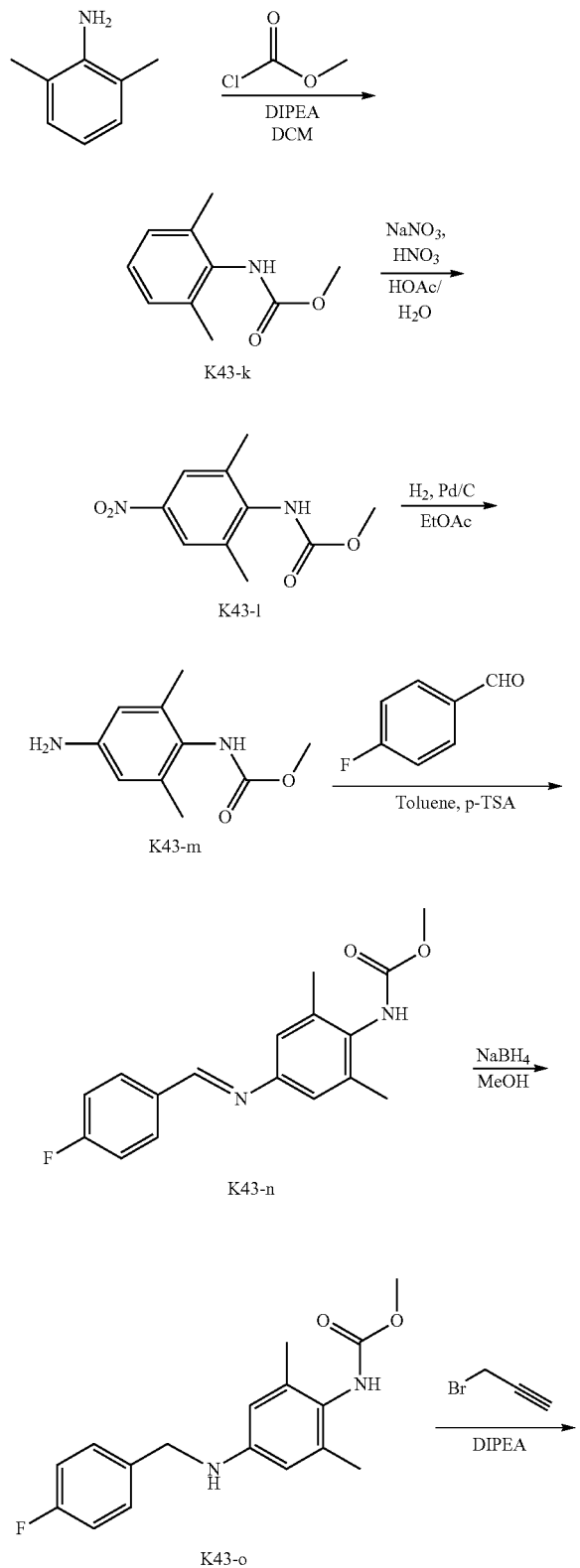

24

2,6-dimethylaniline (40 g, 0.33 mol) was dissolved in dichloromethane (250 mL), and then DIPEA (115 mL, 0.66 mol) was added thereto. Methyl chloroformate (38.35 ml, 0.5 mol) was dropwisely added thereto under ice-water bath. After the addition, the reaction system was naturally warmed to room temperature, and stirred overnight. TLC showed that the reactants were completely reacted. 1% HCl (60 mL) was slowly added into the reaction system, and the reaction system was stirred and layered. The water layer was extracted with dichloromethane. The organic phase was combined, washed with saturated saline, dried with anhydrous sodium sulfate, filtrated and concentrated. The crude product was dissolved in a small amount of dichloromethane, and petroleum ether was dropwisely added thereto to precipitate a solid as the intermediate K43-k (59 g, yield: 88%). $^1$H NMR (300 MHz, CDCl$_3$): δ 7.08 (s, 3H), 6.03 (s, 1H), 3.76 (s, 3H), 2.27 (s, 6H).

The intermediate K43-k (20 g) was dissolved in acetic acid (90 mL), and water (80 mL) and sodium nitrite (19.0, 0.223 mol) were added thereto. Concentrated nitric acid (65%, 55 mL) was dropwisely added under ice-water bath, and the internal temperature of the reaction system was controlled to be not higher than 5° C. After the dropwise addition, the reaction system was slowly warmed to room temperature and stirred for 30 mins, and then heated to 140° C. to reflux for 4 h. After cooled to room temperature, the reaction system was poured into ice-water to quench the reaction. The solid precipitated was filtrated and dried to give an intermediate K43-l (17.8 g, yield 71%). $^1$H NMR (300 MHz, CDCl$_3$): δ 7.964 (s, 1H), 7.082 (s, 1H), 3.786 (s, 3H), 2.364 (s, 3H), 2.265 (s, 3H).

The intermediate K43-l (15 g, 0.067 mol) was dissolved in ethyl acetate (200 mL), and 10% Pd/C (1.5 g) was added thereto under nitrogen atmosphere. After hydrogen was purged three times, the reaction was performed overnight at room temperature. The reaction system was filtrated, and the filtrate was concentrated to give an intermediate K43-m at quantitative yield, which was directly used in the next step.

The intermediate K43-m (13 g, 0.067 mol) was dissolved in toluene (100 mL), p-toluenesulfonic acid (0.38 g, 0.002 mol) and p-fluorobenzaldehyde (12.45 g, 10.8 ml) were added thereto. After the water segregator was equipped, the reaction system was heated to reflux and separate water for 4-5 h. TLC showed that the reaction was completed. The reaction system was concentrated under vacuum to give a crude of the intermediate K43-n, which was directly used in next step. The obtained crude K43-n was dissolved in methanol (150 mL), and sodium borohydride (5.07 g, 0.13 mol) was added thereto in batch under ice-water bath. Then the ice-water bath was removed, and the reaction was performed at room temperature for 1-2 h. TLC showed that the reaction was completed. The reaction system was poured into ice-water bath, and stirred. The solid precipitated was filtrated and dried to give a crude of the intermediate K43-o. The obtained crude of the intermediate K43-o was dissolved in a small amount of dichloromethane, and petroleum ether was dropwisely added thereto to precipitate a nearly white solid, which was filtrated and dried to give the intermediate K43-o (11.1 g, yield in two steps: 55%). $^1$H NMR (300 MHz, CDCl$_3$): δ7.335-7.306 (dd, J=8.7 Hz, 1H), 7.306-7.287 (dd, J=5.7 Hz, 1H), 7.049-7.027 (dd, J=6.6 Hz, 1H), 7.027-6.991 (dd, J=10.8 Hz, 1H), 6.331 (s, 2H), 5.892 (s, 1H), 4.257 (s, 2H), 3.933 (s, 1H), 3.744 (s, 3H), 2.164 (s, 6H).

The intermediate K43-o (10 g, 0.033 mol) was dissolved in DMF (80 mL), and DIPEA (8.54 g, 0.066 mol) and propargyl bromide 2.74 mL, 0.036 mol) were added thereto. The reaction system was reacted at 60° C. for 5 h, and TLC showed that the reaction was completed. The reaction system was poured into water and stirred to precipitate a solid. The solid was filtrated, dried to give a crude of K43, which was dissolved in a small amount of dichloromethane, and petroleum ether was added thereto to precipitate a solid. The solid was filtrated to give K43 (9.8 g, yield: 87%). The $^1$H NMR thereof was consistent with that of K43 prepared in Preparation Example 1.

Preparation Example 3

Preparation Example 3.1, Synthesis of methyl 4-(N-parafluorobenzyl-N-propargyl-amino) phenylaminothioformate (K43)

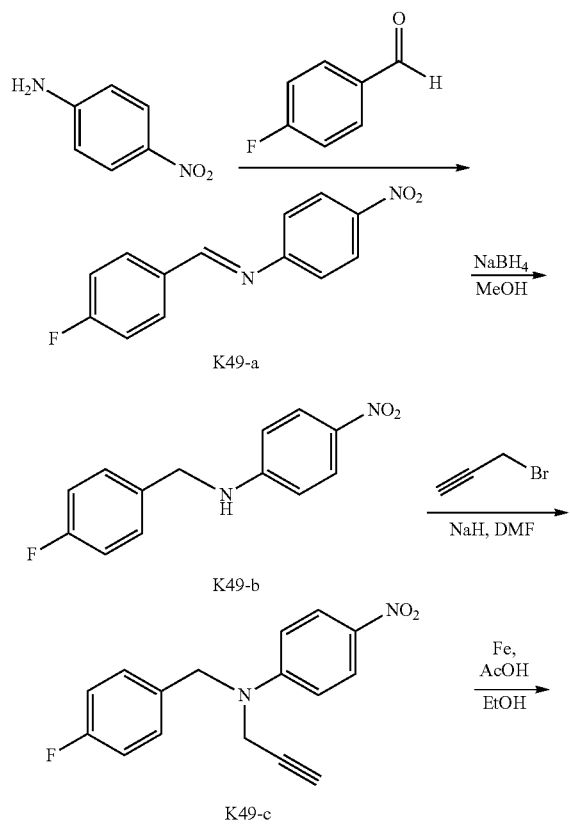

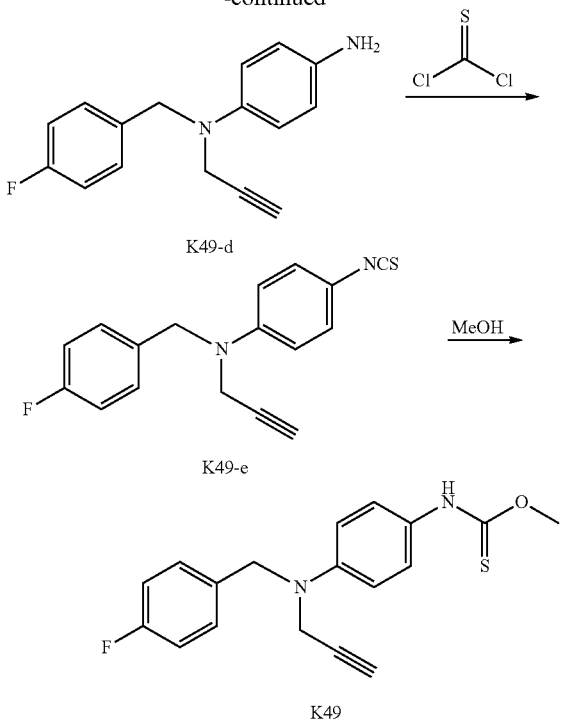

p-nitroaniline (2.76 g, 20.0 mmol) and p-fluorobenzaldehyde (2.1 mL, 20.0 mmol) were added into a 150 mL three necked flask, toluene (60 mL) was added thereto and the reaction was refluxed and water was separated with water segregator for 3 h. After cooled to room temperature, the reaction system was concentrated under vacuum to remove toluene. The obtained intermediate K49-a was redissolved in methanol (40 mL), NaBH$_4$ (1.52 g, 40.0 mmol) was added thereto in batch under vigorously stirring, and the reaction was preformed at room temperature for 3 h. Crushed ice was added to quench the reaction, and water (30 mL) was added under vigorously stirring to precipitate a large amount of solid, which was suction-filtrated. The filter cake was washed with anhydrous ethylether (10 mL) twice to give a product K49-b (3.4 g, yield: 70%, yellow solid). $^1$H NMR (300 MHz, CDCl$_3$): δ 8.08 (d, J=9.3 Hz, 2H), 7.31 (dd, J$_1$=5.4 Hz, J$_2$=8.4 Hz, 2H), 7.06 (t, J=8.7 Hz, 2H), 6.57 (d, J=9.3 Hz, 2H), 4.86 (s, 1H), 4.41 (d, J=2.7 Hz, 2H).

K49-b (3.4 g, 14.0 mmol) was dissolved in DMF (40 mL), NaH (616 mg, 15.4 mmol) was quickly added under ice bath, and the reaction was preformed at room temperature for 0.5 h. Propargyl bromide (1.22 mL, 15.4 mmol) was added, and the reaction was preformed at 65° C. for 4 h. Ethyl acetate (80 mL) was dropwisely added into the reaction system. The mixture was transferred to a separating funnel and washed with water (40 mL) twice. The organic phase was combined and washed with saturated saline (30 mL) once, dried with anhydrous sodium sulfate, and concentrated. and the residue was purified with column chromatography (PE/EA=8:1) to give K49-c (3.4 g, yield: 86%). $^1$H NMR (300 MHz, CDCl$_3$): δ 8.14 (d, J=9.0 Hz, 2H), 7.26 (dd, J=5.4, 8.4 Hz, 2H), 7.04 (t, J=8.7 Hz, 2H), 6.79 (d, J=9.3 Hz, 2H), 4.68 (s, 2H), 4.17 (d, J=2.1 Hz, 2H), 2.32 (t, J=2.1 Hz, 1H).

The obtained K49-c (3.4 g, 12.0 mmol) was dissolved in anhydrous ethanol (50 mL), glacial acetic acid (3.0 mL) and iron powder (1.3 g) were added thereto and the mixture was refluxed for 4 h. The mixture was filtrated to remove the unreacted iron powder. The filtrate was concentrated to nearly dryness and the residue was redissolved in ethyl acetate (70 mL) and transferred to a separating funnel. The mixture was washed with saturated aqueous sodium bicarbonate solution (20 mL) once, and with water (40 mL) twice. The organic phase was combined and washed with saturated saline (30 mL) once, dried with anhydrous sulfate, and concentrated to remove solvent. The residue was purified with silica gel column chromatography (petroleum ether/ethyl acetate=4:1, 3:1) to give K49-d (1.95 g, yield: 64%, brown solid). $^{13}$C NMR (75 MHz, CDCl$_3$): δ 162.3 (J=243.3 Hz), 142.4, 140.2, 134.6, 129.8 (J=8.0 Hz), 118.9, 116.5, 115.5 (J=21.1 Hz), 80.0, 73.0, 55.6, 41.4.

K49-d (508 mg, 2.0 mmol) was dissolved in dichloromethane (10 mL), triethylamine (750 μL, 5.2 mmol) was added, thiophosgene (300 μL, 2.6 mmol) was dropwisely added under ice bath and the mixture was reacted at room temperature for 3 h. The mixture was concentrated to remove solvent, and the residue was purified with silica gel column chromatography (petroleum ether/ethyl acetate=10:1) to give K49-e (576 mg, yield: 96.0%, yellow oil). $^1$H NMR (300 MHz, CDCl$_3$): δ 7.24 (dd, J=8.4, 5.4 Hz, 2H), 7.12 (d, J=9.3 Hz, 2H), 7.03 (t, J=8.7 Hz, 2H), 6.78 (d, J=9.3 Hz, 2H), 4.53 (s, 2H), 4.03 (d, J=2.1 Hz, 2H), 2.25 (t, J=2.1 Hz, 1H).

K49-e (150 mg, 0.5 mmol) was dissolved in methanol (5 mL) and the mixture was refluxed overnight. The mixture was concentrated to remove solvent, and the obtained crude was purified with silica gel column chromatography (petroleum ether/ethyl acetate=8:1) to give K49 (142 mg, yield: 87.0%, yellow oil). $^1$H NMR (300 MHz, CDCl$_3$): δ 8.40 (brs, 1H), 7.24 (dd, J=8.4, 5.4 Hz, 2H), 7.11 (d, J=9.3 Hz, 2H), 7.02 (d, J=9.3 Hz, 2H), 6.82-6.85 (m, 2H), 4.50 (s, 2H), 4.10 (s, 3H), 3.93 (d, J=2.1 Hz, 2H), 2.24 (t, J=2.1 Hz, 1H).

Preparation Example 3.2, Synthesis of methyl 4-(N-parafluorobenzyl-N-propargyl-amino)-3-fluorophenylaminothioformate (K50)

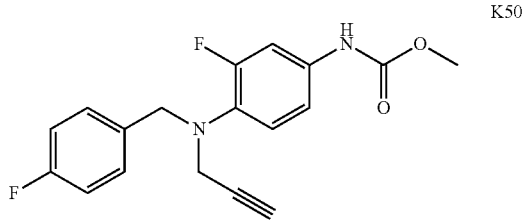 [SMILES: C#CCN(Cc1ccc(F)cc1)c1ccc(NC(=O)OC)cc1F]

K50

K50 was prepared in the similar manner as that in Preparation Example 3.2 $^1$H NMR (CDCl$_3$, 300 MHz): δ 8.25 (brs, 1H), 7.38 (dd, J=5.4, 8.4 Hz, 2H), 7.09-7.15 (m, 2H), 7.02 (t, J=9.3 Hz, 2H), 4.28 (s, 2H), 4.12 (brs, 3H), 3.93 (d, J=2.1 Hz, 2H), 2.27 (t, J=2.1 Hz, 1H).

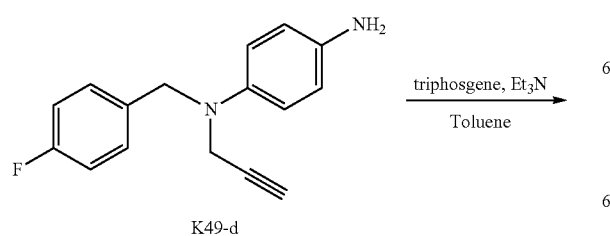

K49-d

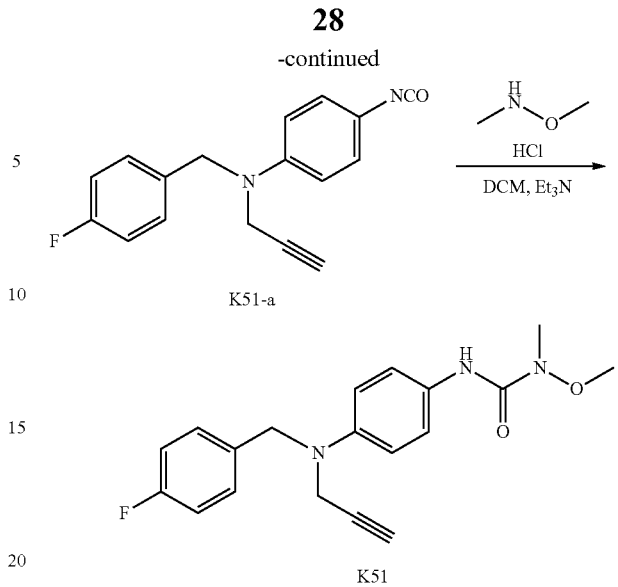

K51-a

K51

K49-d (508 mg, 2.0 mmol) was dissolved in anhydrous toluene (10 mL), triethylamine (1.07 mL, 6.0 mmol) and triphosgene (356 mg, 1.2 mmol) were added thereto, and the mixture was reacted under refluxing for 3 h. The mixture was concentrated to remove solvent, and the obtained residue was purified with silica gel column chromatography (petroleum ether/ethyl acetate=10:1) to give K51-a (536 mg, yield: 96%, yellow solid).

K51-a (84 mg, 0.3 mmol) and N,O-dimethylhydroxylamine hydrochloride (35 mg, 0.36 mmol) was dissolved in anhydrous toluene (5 mL), triethylamine (82 μL, 0.6 mmol) was further added thereto and the mixture was reacted at room temperature overnight. The mixture was concentrated to remove solvent, and the obtained residue was purified with silica gel column chromatography (petroleum ether/ethyl acetate=8:1) to give K51 (90 mg, yield: 88%, yellow oil). $^1$H NMR (300 MHz, CDCl$_3$): δ 7.54 (brs, 1H), 7.32 (dd, J=8.4, 5.4 Hz, 2H), 7.24 (d, J=9.3 Hz, 2H), J=8.4 Hz, 2H), 6.89 (d, J=9.3 Hz, 2H), 4.45 (s, 2H), 3.94 (d, J=2.1 Hz, 2H), 3.75 (s, 3H), 3.17 (s, 3H), 2.21 (t, J=2.1 Hz, 1H).

Preparation Example 4

Preparation Example 4.1, Synthesis of N-[4-(N-p-fluorobenzyl-N-propargyl-amino)-phenyl]-2-methoxyacetamide (K52)

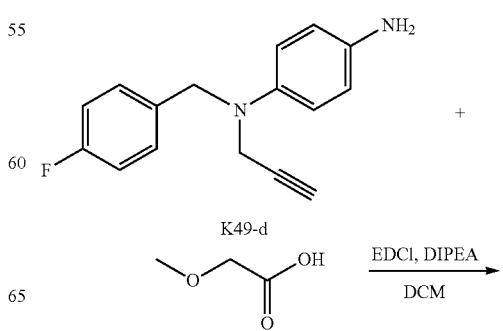

K49-d

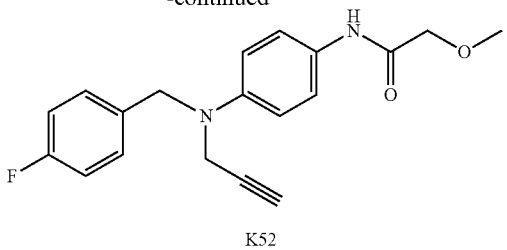

K52

K49-d (100 mg, 0.4 mmol) and methoxyacetic acid (34 μL, 0.44 mmol), 1-ethyl-3-(3-dimethylaminopropyl)carbodiimide hydrochloride (EDCI, 92 mg, 0.48 mmol) were dissolved in anhydrous dichloromethane (5 mL), DIPEA (107 μL, 0.6 mmol) was further added thereto and the mixture was reacted at room temperature for 4 h. After 20 mL of ethyl acetate was added, the reaction system was transferred to a separating funnel and washed with water (10 mL) twice. The organic phase was combined and washed with saturated saline (10 mL) once, dried with anhydrous sulfate, and concentrated to remove solvent. The obtained residue was purified with silica gel column chromatography (petroleum ether/ethyl acetate=8:1) to give K52 (104 mg, yield: 80%). $^1$H NMR (300 MHz, CDCl$_3$): δ 8.10 (s, 1H), 7.43 (d, J=9.0 Hz, 2H), 7.27 (dd, J=5.4, 8.4 Hz, 2H), 7.02 (t, J=8.7 Hz, 2H), 6.86 (d, J=9.0 Hz, 2H), 4.47 (s, 2H), 4.00 (s, 3H), 3.96 (d, J=2.1 Hz, 2H), 3.49 (s, 3H), 2.22 (t, J=2.1 Hz, 1H). $^{13}$C NMR (75 MHz, CDCl$_3$): δ 167.4, 162.3 (J=243.6 Hz), 146.1, 134.1, 134.0, 129.2 (J=8.0 Hz), 121.7, 115.8 (J=21.6 Hz), 115.6, 79.6, 72.7, 72.3, 59.5, 54.9, 40.5. HR-ESIMS (m/z): calculated for C$_{19}$H$_{20}$FN$_2$O$_2$ [M+H]$^+$ 327.1509, found: 327.1501.

Preparation Example 4.2, the Following Compounds were Prepared in the Similar Manner as that in Preparation Example 1 by Reacting with an Acid Corresponding to the Product, Starting from K49-d

| K53 | 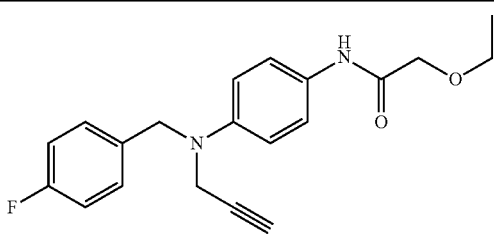 | 8.15 (s, 1H), 7.43 (d, J = 9.3 Hz, 2H), 7.28 (dd, J = 8.4, 5.4 Hz, 2H), 7.02 (t, J = 8.7 Hz, 2H), 6.87 (d, J = 9.0 Hz, 2H), 4.47 (s, 2H), 4.04 (s, 2H), 3.96 (d, J = 2.1 Hz, 2H), 3.64 (q, J = 6.9 Hz, 2H), 2.22 (t, J = 2.1 Hz, 1H), 1.30 (t, J = 6.9 Hz, 3H). |
|---|---|---|
| K54 | 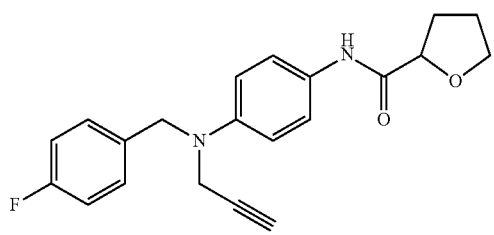 [SMILES: C#CCN(Cc1ccc(F)cc1)c1ccc(NC(=O)C2CCCO2)cc1] | 8.32 (s, 1H), 7.45 (d, J = 9.0 Hz, 2H), 7.29 (dd, J = 8.4, 5.4 Hz, 2H), 7.01 (t, J = 8.7 Hz, 2H), 6.86 (d, J = 9.0 Hz, 2H), 4.46 (s, 2H), 3.96-4.03 (m, 5H), 2.32-2.38 (m, 1H), 2.14-2.23 (m, 2H), 1.90-1.95 (m, 2H). |
| K55 | 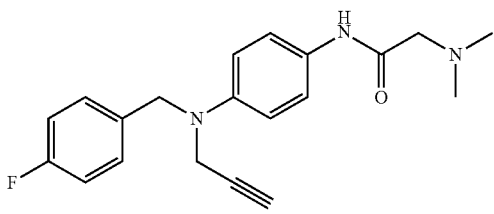 [SMILES: C#CCN(Cc1ccc(F)cc1)c1ccc(NC(=O)CN(C)C)cc1] | 8.92 (s, 1H), 7.46 (d, J = 9.0 Hz, 2H), 7.28 (dd, J = 8.7, 5.4 Hz, 2H), 7.01 (t, J = 8.7 Hz, 2H), 6.87 (d, J = 9.0 Hz, 2H), 4.46 (s, 2H), 3.96 (d, J = 2.1 Hz, 2H), 3.05 (s, 2H), 2.36 (s, 6H), 2.22 (t, J = 2.1 Hz, 1H). |
| K56 | 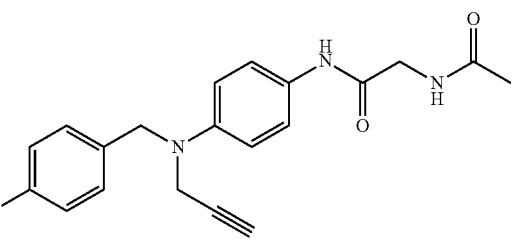 | 8.51 (s, 1H), 7.38 (d, J = 9.0 Hz, 2H), 7.26 (dd, J = 8.7, 5.4 Hz, 2H), 7.01 (t, J = 8.7 Hz, 2H), 6.84 (d, J = 9.0 Hz, 2H), 6.71 (s, 1H), 4.45 (s, 2H), 4.08 (d, J = 5.1 Hz, 2H), 3.95 (d, J = 2.1 Hz, 2H), 2.21 (t, J = 2.1 Hz, 1H), 2.01 (s, 3H). |

| | | |
|---|---|---|
| K57 | 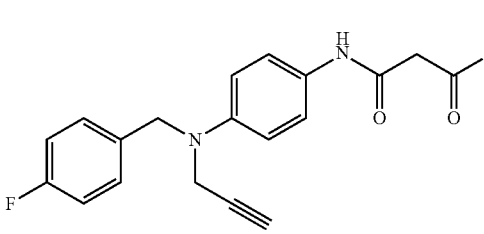 | 8.95 (s, 1H), 7.42 (d, J = 9.0 Hz, 2H), 7.29 (dd, J = 8.4, 5.4 Hz, 2H), 7.01 (t, J = 8.7 Hz, 2H), 6.84 (d, J = 9.0 Hz, 2H), 4.47 (s, 2H), 3.97 (d, J = 2.1 Hz, 2H), 3.79 (s, 3H), 3.46 (s, 2H), 2.22 (t, J = 2.1 Hz, 1H). |
| K58 | 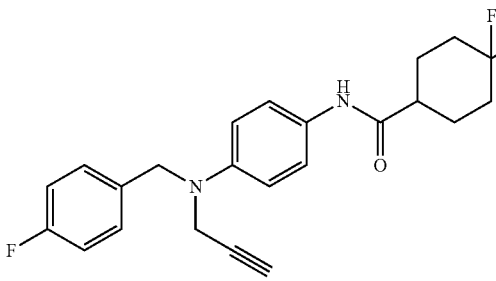 | 7.37 (d, J = 9.3 Hz, 2H), 7.27 (dd, J = 8.4, 5.4 Hz, 2H), 7.01 (t, J = 8.7 Hz, 2H), 6.84 (d, J = 9.0 Hz, 2H), 4.46 (s, 2H), 3.96 (d, J = 2.1 Hz, 2H), 2.18-2.36 (m, 4H), 1.68-2.06 (m, 6H). |

Preparation Example 5, Synthesis of methyl 4-(N-parafluorobenzyl-N-3,3-dideuteriumpropargyl-amino)phenylaminothioformate (K47)

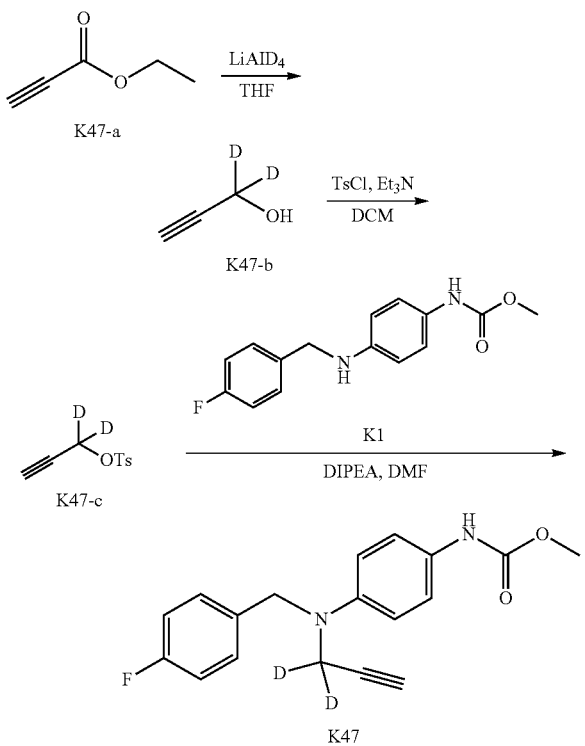

K47-a (0.51 mL, 5.0 mmo) was dissolved in anhydrous tetrahydrofuran (THF) (10 mL), aluminium lithium deuteride solution (157.5 mg, 3.75 mmol) was slowly added thereto under dry ice-acetone bath, and the mixture was warmed to −40° C. and kept at such temperature for 5 h. The reaction was quenched by using 0.5 mL of methanol, and warmed to room temperature, and then quenched with aqueous ammonium chloride solution. The reaction system was extracted with ethylether (20 mL), and the obtained organic phase was washed with water (15 mL) twice, and with saturated saline (10 mL) once, dried with anhydrous sodium sulfate and carefully concentrated to about 1 mL. The obtained intermediate K47-b was directly used in the next step.

The intermediate K47-b obtained above was dissolved in dichloromethane (10 mL), p-toluenesulfonyl chloride (1.15 g, 6 mmol) and triethylamine (0.82 mL, 6 mmol) were added under ice bath, and the mixture was kept at the temperature for 2 h. The reaction system was poured into crushed ice, and extracted with ethylether. The obtained organic phase was washed with water (20 mL) twice and concentrated, and the crude product was purified by silica gel column chromatography (petroleum ether/ethyl acetate=8:1) to give an intermediate, 4-toluenesulfonate K47-c (80 mg, yield: 13%, yellow solid). $^1$H NMR (300 MHz, CDCl$_3$): δ 7.82 (d, J=8.4 Hz, 2H), 7.35 (d, J=8.4 Hz, 2H), 2.45 (s, 3H), 2.04 (s, 1H).

K1 was prepared according to the method of Preparation method 1 of WO2013060097. 4-toluenesulfonate K47-c (40 mg, 0.19 mmol) and K1 (52 mg, 0.19 mmol) were dissolved in DMF (3 mL), and then DIPEA (0.175 mL, 1.0 mmol) was added thereto. After the reaction was preformed at 65° C. for 4 h, ethyl acetate (20 mL) was dropwisely added into the reaction system. The mixture was transferred to a separating funnel and washed with water (15 mL) twice. The obtained organic phase was further washed with saturated saline (10 mL) once, dried with anhydrous sodium sulfate and concentrated. The obtained K47 crude was purified with silica gel column chromatography (petroleum ether/ethyl acetate=8:1) to give K47 (55 mg, yield: 92%, yellow oil). $^1$H NMR (300 MHz, CDCl$_3$): δ 7.25-7.31 (m, 4H), 7.02 (t, J=8.7 Hz, 2H), 6.85 (d, J=8.7 Hz, 2H), 6.68 (s, 1H), 4.44 (s, 2H), 3.75 (s, 3H), 2.23 (s, 1H).

Preparation Example 6, Synthesis of methyl 4-(N-parafluorobenzyl-N-3-cyclopropyl propargyl-amino) phenylaminothioformate (K59)

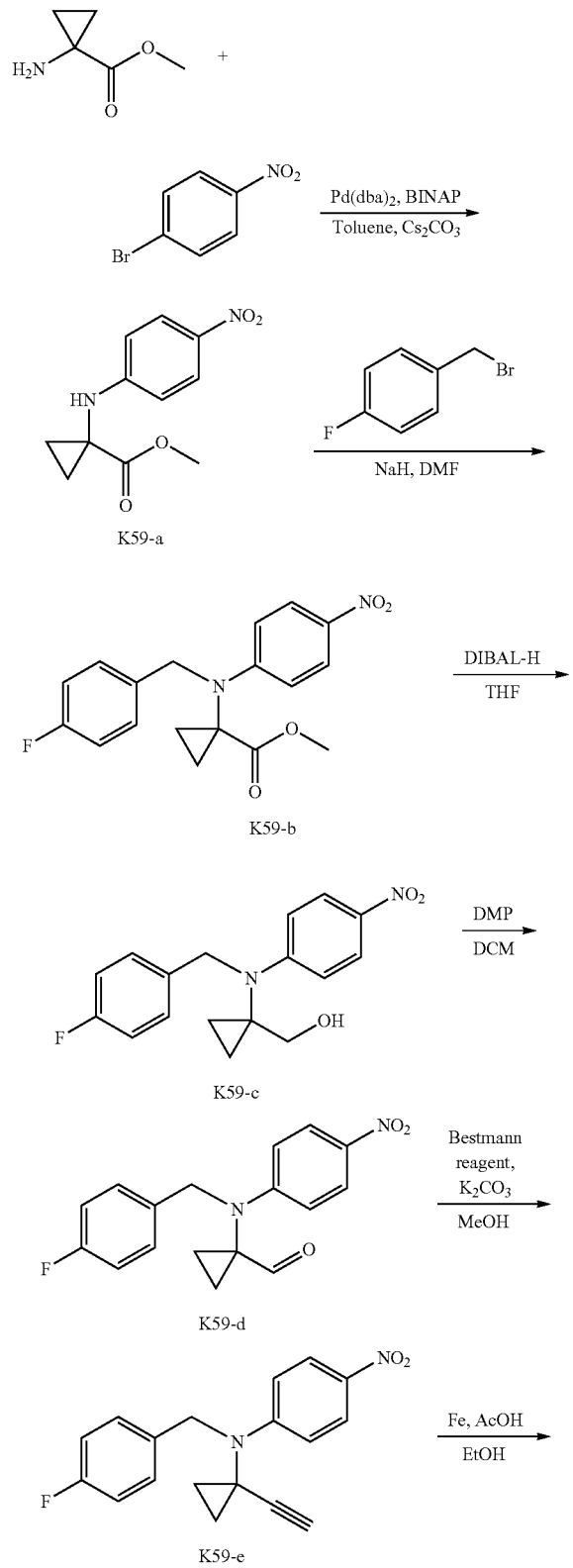

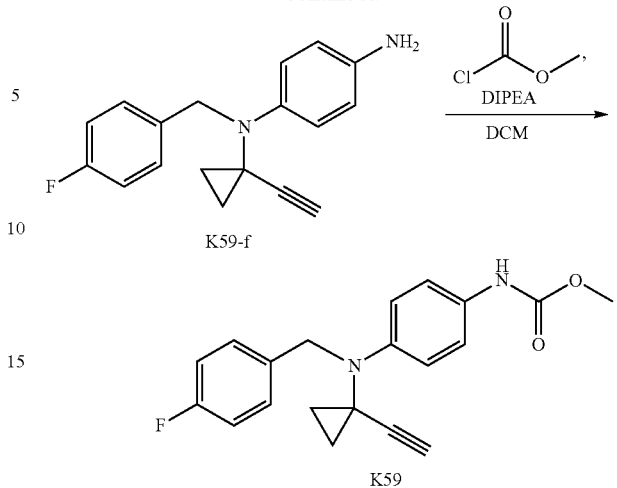

Methyl aminocyclopropylcarboxylate (690 mg, 6 mmol), cesium carbonate (3.90 g, 12 mmol), 2,2'-bis(diphenylphosphino)-1,1'-binaphthalene (BINAP, 124 mg, 0.2 mmol), and p-bromonitrobenzene (1.2 g, 6 mmol) were dissolved in anhydrous toluene (50 mL). After the inside atmosphere of the reactor was completely replaced with argon, Bis(dibenzylideneacetone)palladium(Pd(dba)$_2$, 182 mg, 0.2 mmol) as a catalyst was quickly added, and the mixture was heated to reflux for 6 h. After the reaction mixture was cooled to room temperature, ethyl acetate (60 mL) was dropwisely added thereto. The obtained organic phase was washed with water (30 mL) twice, and with saturated saline (10 mL) once, dried with anhydrous sodium sulfate, and concentrated to remove solvent. The obtained crude was purified with silica gel column chromatography (petroleum ether/ethyl acetate=10:1) to give an intermediate K59-a (1.06 g, yield: 75%, brown solid). $^1$H NMR (300 MHz, CDCl$_3$): δ 8.10 (d, J=8.7 Hz, 2H), 6.67 (d, J=8.7 Hz, 2H), 5.11 (brs, 1H), 3.74 (s, 3H), 1.68-1.72 (m, 2H), 1.20-1.24 (m, 2H).

The intermediate K59-a (1.06 g, 4.5 mmol) was dissolved in DMF (20 mL), NaH (216 mg, 5.4 mmol) was quickly added thereto under ice bath and then the ice bath was removed and the mixture was reacted at room temperature for 1 h. Then p-fluorobenzyl bromide (0.622 mL, 5.0 mmol) was added, and the obtained mixture was reacted at 65° C. for 3 h. Ethyl acetate (40 mL) was added into the reaction system, and the obtained organic phase was washed with water (30 mL) twice, and with saturated saline (30 mL) once, dried with anhydrous sodium sulfate and concentrated to remove solvent. The obtained crude was purified with silica gel column chromatography (petroleum ether/ethyl acetate=12:1) to give K59-b (1.20 g, yield: 83%).

The intermediate K59-b (340 mg, 1.0 mmol) was dissolved in anhydrous tetrahydrofuran (10 mL), and diisobutylaluminium hydride (DIBAL-H, 1M solution in THF, 1.6 mL, 1.6 mmol) was dropwisely added thereto under dry ice-acetone bath, and the obtained mixture was kept at the temperature for 5 h. After that, 0.5 mL of methanol was added into the mixture to quench the reaction. After the mixture was warmed to room temperature, 20 mL of ethyl acetate was dropwisely added thereto. The obtained mixture was washed with 1M aqueous HCl solution (10 mL) once, with water (15 mL) twice and with saturated saline (10 mL) once, respectively. Then the organic phase was dried with anhydrous sulfate, and concentrated to remove solvent. The crude was purified with silica gel column chromatography (petroleum ether/ethyl acetate=6:1) to give an intermediate K59-c (177 mg, yield: 56%, oil). $^1$H NMR (300 MHz, CDCl$_3$): δ 7.99 (d, J=9.3 Hz, 2H), 6.96-7.02 (m, 4H), 6.74 (d, J=9.7 Hz, 2H), 4.73-4.94 (m, 2H), 4.21 (brs, 1H), 3.48 (brs, 1H), 1.23-1.27 (m, 4H).

The intermediate K59-c (177 mg, 0.56 mmol) was dissolved in dichloromethane (5 mL), and Dess-Martin periodinane (DMP, 367 mg, 0.84 mmol) was added thereto. After kept at room temperature for 4 h, the mixture was concentrated, and the residue was purified with silica gel column chromatography (petroleum ether/ethyl acetate=10:1) to give an intermediate K59-d (150 mg, yield: 85%, yellow solid). $^1$H NMR (300 MHz, CDCl$_3$): δ 9.11 (s, 1H), 8.05 (d, J=10.5 Hz, 2H), 6.99-7.11 (m, 4H), 6.68 (d, J=10.5 Hz, 2H), 4.87 (d, J=17.4 Hz, 1H), 4.65 (d, J=17.4 Hz, 1H), 1.95-2.00 (m, 1H), 1.51-1.63 (m, 3H).

The intermediate K59-d (150 mg, 0.48 mmol) and anhydrous potassium carbonate (K$_2$CO$_3$) (132 mg, 0.96 mmol) were dissolved in methanol (5 mL), and Bestmann reagent (dimethyl diazomethylphosphonate, 110 mg, 0.58 mmol) was added thereto. After kept at room temperature overnight, the mixture was concentrated and the obtained residue was redissolved in ethyl acetate (20 mL). The obtained solution was washed with water (15 mL) twice, and with saturated saline (10 mL) once respectively, and dried with anhydrous sodium sulfate, and concentrated to remove solvent. The obtained crude was purified with silica gel column chromatography (petroleum ether/ethyl acetate=8:1) to obtain an intermediate K59-e (106 mg, yield: 71%, brown solid). $^1$H NMR (300 MHz, CDCl$_3$): δ 8.10 (d, J=9.3 Hz, 2H), 7.09-7.12 (m, 2H), 6.98-7.04 (m, 2H), 6.92 (d, J=9.3 Hz, 2H), 4.75 (s, 2H), 2.19 (s, 1H), 1.21-1.25 (m, 4H).

The intermediate K59-e (106 mg, 0.34 mmol) was dissolved in anhydrous ethanol (5 ml), glacial acetic acid (0.2 mL) and iron powder (60 mg) were added thereto, and the reaction system was refluxed for 3 h. The mixture was filtrated to remove unreacted iron powder, and the filtrate was sufficiently concentrated and the residue was redissolved in 20 mL of ethyl acetate. The obtained solution was washed with saturated aqueous sodium bicarbonate solution (10 mL) once, with water (15 mL) twice, and with saturated saline (10 mL) once respectively, and dried with anhydrous sodium sulfate. and concentrated to remove solvent. The obtained crude was purified with silica gel column chromatography (petroleum ether/ethyl acetate=6:1, 4:1) to obtain an intermediate K59-f (82 mg, yield: 86%, yellow solid). $^1$H NMR (300 MHz, CDCl$_3$): δ 7.20 (dd, J=8.4, 5.4 Hz, 2H), 6.98 (t, J=8.4 Hz, 2H), 6.84 (d, J=9.3 Hz, 2H), 6.60 (d, J=9.3 Hz, 2H), 4.50 (s, 2H), 3.36 (brs, 2H), 2.14 (s, 1H), 1.18-1.20 (m, 2H), 1.04-1.07 (m, 2H).

The intermediate K59-f (82 mg, 0.28 mmol) was dissolved in dichloromethane (5 mL), DIPEA (0.10 mL, 0.56 mmol) was added thereto, and methyl chloroformate (34 μL, 0.44 mmol) was dropwisely added under ice bath. After addition, the mixture was kept at room temperature for half an hour. Into the above reaction system, 10 mL of ethyl acetate was added dropwisely, and the obtained organic phase was washed with water (10 mL) twice, and with saturated saline (10 mL) once, respectively, dried with anhydrous sodium sulfate, and then concentrated to remove solvent. The obtained crude was purified with silica gel column chromatography (petroleum ether/ethyl acetate=6:1) to give K59 (82 mg, yield: 91%, yellow oil). $^1$H NMR (300 MHz, CDCl$_3$): δ 7.15-7.21 (m, 4H), 6.98 (t, J=8.4 Hz, 2H), 6.88 (d, J=9.0 Hz, 2H), 6.38 (s, 1H), 4.59 (s, 2H), 3.74 (s, 3H), 2.13 (s, 1H), 1.26-1.29 (m, 2H), 1.10-1.14 (m, 2H). $^{13}$C NMR (75 MHz, CD$_3$OD): δ 162.1 (J=147.8 Hz), 155.2, 144.6, 135.9, 131.3, 128.3 (J=6.0 Hz), 120.2, 115.8, 114.9 (J=21.0 Hz), 84.8, 68.4, 55.9, 51.3, 42.6, 18.8. HR-ESIMS (m/z): calculated for C$_{20}$H$_{20}$FN$_2$O$_2$ [M+H]$^+$ 339.1509, found: 339.1505.

Preparation Example 7: Synthesis of methyl 4-(N-parafluorobenzyl-N-propargyl-amino)-2,6-dimethyl-phenylaminoformate hydrochloride (K43.HCl)

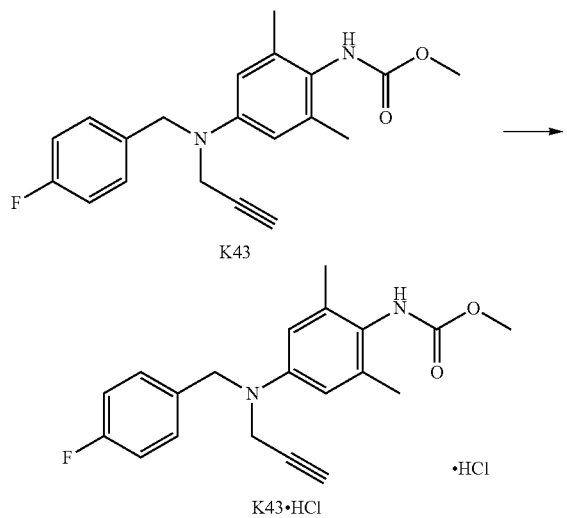

Methyl 4-(N-parafluorobenzyl-N-propargyl-amino)-2,6-dimethylphenylaminoformate (K43, 510 mg, 1.5 mmol) was dissolved in dichloromethane (5 mL), and a hydrogen chloride solution in ethyl acetate (5N, 1 mL) was added thereto. The mixture was stirred for 10 mins, and then concentrated to remove solvent to give methyl 4-(N-parafluorobenzyl-N-propargyl-amino)-2,6-dimethylphenylaminoformate hydrochloride (K43.HCl) (565 mg).

The hydrochlorides of other compounds can be obtained by using a method similar to that of Preparation example 7.

II. Electrophysiological Experimental Examples

Electrophysiological Experimental Example 1: The Cell Lines Used in the Electrophysiological Experiment was Chinese Hamster Ovary Cell Line; KCNQ cDNA was Transformed into *E. coli* and Expressed in *E. coli*, and then Confirmed by Plasmid Extraction and Sequencing 1. Cell Culture and Transfection The culture medium for Chinese hamster oocytes (CHO-K1) (Culture Collection of Chinese Academy of Sciences): 50/50 DMEM/F-12 (Cellgro, Manassas, Va.), added with 10% fetal bovine serum (FBS) (Gibco, Australia) and 2 mM L-glutamic acid (Invitrogen). Expression of KCNQ channels: 24 h before transfection, CHO-K1 spreaded on a dish with a diameter of 60 mm. Lipofectamine 2000™ agent (Invitrogen) was used for Transfection according to the protocol thereof. GFP (green fluorescent protein) was cotransfected to be used as a indication of successful converting into KCNQ plasmid.

2. Electrophysiological Recordings in CHO Cells

Whole-cell voltage-clamp recording was performed on an Axopatch-200B amplifier (Molecular Devices, Sunnyvale, Calif.) at room temperature. The electrode was made by drawing borosilicate glass capillary (World Precision Instruments, Sarasota, Fla.). The electric resistance of the electrode filled with an intracellular fluid is 3 to 5 MΩ. The composition of the intracellular fluid (1 L) was as follows: 145 mM KCl(Sigma), 1 mM $MgCl_2$(Sigma), 5 mM EGTA (Sigma), 10 mM HEPES(Sigma) and 5 mM MgATP(Sigma) (pH was adjusted to 7.3 with KOH). During the recording, an extracellular fluid was continuously perfused by using a BPS perfusion system (ALA Scientific Instruments, Westburg, N.Y.). The composition of the extracellular fluid (1 L) was as follows: 140 mM NaCl(Sigma), 5 mM KCl(Sigma), 2 mM $CaCl_2$(Sigma), 1.5 mM $MgCl_2$(Sigma), 10 mM HEPES(Sigma) and 10 mM glucose(Sigma) (pH was adjusted to 7.4 with NaOH). Electric signal was filtered at 1 kHz and further converted into digital signal by using pClamp 9.2 software (Molecular Devices, Sunnyvale, Calif.) in DigiData 1322A. Series resistors compensate 60 to 80%. Up to date, multivoltage scheme was generally adopted, wherein the clamp voltage was set at −80 mV, stimulating voltage was a gradient voltage from −90 mV to 60 mV with interval of 10 mV, and the stimulating time for each voltage was 2000 ms.

3. Experimental Results $V_{1/2}$ is the voltage at which 50% of cells were activated, $\Delta V_{1/2}$ is the shift amount of $V_{1/2}$, negative sign (−) represents a left-ward shift of the current activation curve. $I/I_0$ represents the current enhancement factor, wherein, $I_0$ is the maximum induced current produced under stimulation of −10 mV testing voltage after administrating cells with blank extracellular fluid, I is the maximum induced current produced under stimulation of −10 mV testing voltage after administrating the drug (the compound concentration was 10 μM), $I/I_0 > 1$ represents activating activity, and $I/I_0 < 1$ represents inhibiting activity. N is the number of tested cells. NT represents non-tested.

| Compound | $\Delta V_{1/2}$ (mV) | $I/I_0$ | N |
|---|---|---|---|
| K40•HCl | −3.42 ± 1.54 | 1.40 ± 0.04 | 3 |
| K41•HCl | −23.28 ± 1.37 | 4.8 ± 0.73 | 3 |
| K42•HCl | −5.2 ± 0.7 | 0.52 ± 0.01 | 3 |
| K43•HCl | −38.52 ± 1.67 | 4.75 ± 1.29 | 3 |
| K44•HCl | 13.47 ± 2.13 | 0.72 ± 0.05 | 3 |
| K45•HCl | −5.1 ± 0.9 | 0.57 ± 0.01 | 3 |
| K46•HCl | −6.5 ± 2.1 | 1.52 ± 0.55 | 3 |
| K47•HCl | −18.10 ± 0.03 | 2.10 ± 0.08 | 3 |
| K48•HCl | −13.2 ± 1.5 | 1.24 ± 0.16 | 3 |
| K49•HCl | −22 ± 2.5 | 4.4 ± 1.6 | 3 |
| K50•HCl | −9.06 ± 0.15 | 1.39 ± 0.12 | 3 |
| K51•HCl | −8.89 ± 1.12 | 1.61 ± 0.08 | 5 |
| K52•HCl | −10.93 ± 1.86 | 5.80 ± 0.52 | 5 |
| K53•HCl | −14.81 ± 0.92 | 7.31 ± 1.09 | 5 |
| K54•HCl | −30.9 ± 4.1 | 7.55 ± 1.92 | 5 |
| K55•HCl | −10.76 ± 4.51 | 1.72 ± 0.14 | 3 |
| K56•HCl | −2.0 ± 1.3 | 1.10 ± 0.10 | 3 |
| K57•HCl | −31.55 ± 0.86 | 8.13 ± 2.57 | 3 |
| K58•HCl | −33.68 ± 1.05 | 1.78 ± 0.19 | 3 |
| K59•HCl | −0.14 ± 2.33 | 1.01 ± 0.13 | 3 |

Results and discussion: from the above electrophysiological Experimental results, it can be seen that the compounds disclosed in present invention not only well retains the agonistic activity on KCNQ potassium channel, but also some compounds according to present invention have a significantly improved current enhancement factor ($I/I_0$) than that of K21 disclosed in WO2013060097 ($I/I_0$=1.53±0.15).

Electrophysiological Experimental Example 2:
Comparison of Agonistic Activity of K43 and RTG on KCNQ2 Homotetramer Channel The experimental procedure was the same as that in Electrophysiological Example 1. The assay for KCNQ2 channel dose-response curve (DRC) was performed on CHO-K1 cells transfected with KCNQ2 plasmid; and the assay for KCNQ2/3 heterotetramer channel DRC was performed on CHO-K1 cells cotransfected with KCNQ2 and KCNQ3 plasmids. Dose-response curve was fitted by using Boltzmann equation (Boltzmann sigmoidal), and the results were shown in FIG. 1.

Results and discussion: in FIG. 1, $EC_{50}$=1.53 nM (K43), $EC_{50}$=1.32 μM (RTG). From the comparison results of DRCs in FIG. 1, it can be seen that the agonistic activity of K43 on KCNQ2 homotetramer channel was more than 800 times of that of RTG, and the agonistic activity of K43 was much higher than that of RTG.

Electrophysiological Experiment Example 3:
Comparison of Agonistic Activity of K43, CF341
(i.e, K21 Disclosed in WO2013060097) and RTG on KCNQ2/3 Heterotetramer Channel The experimental procedure was the same as that in Electrophysiological Example 1. KCNQ2/3 heterotetramer channel is based on 4 ng plasmid per 10 μL Lipo2000. KCNQ2 and KCNQ3 plasmid were cotransfected at a mass ratio of 1:1. 24 h after transfection, CKO-K1 cells were lysed with trypsin(Sigma, China) and re-spreaded on a dish with a diameter of 60 mm which was laid with poly-L-lysine (Sigma)-immersed slides thereon. The assay for KCNQ2/3 heterotetramer channel DRC was performed on CHO-K1 cells cotransfected with KCNQ2 and KCNQ3 plasmids. DRC was fitted by using Boltzmann equation (Boltzmann sigmoidal), and results were shown in FIG. 2.

Figure 2:
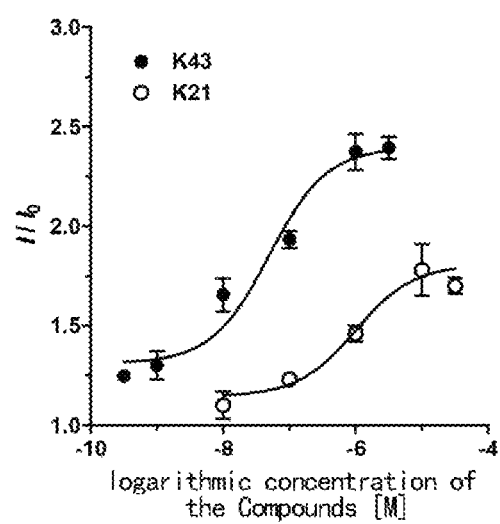
FIG. 2 is a graph showing the dose-response curves of K43 according to present invention and k21 on KCNQ2/3 heterotetramer channel.

Results and discussion: in FIG. 2, $EC_{50}$=49 nM (K43), $EC_{50}$=1.9 μM (K21). From the comparison of DRCs in FIG. 2, it can be seen that the agonistic activity of K43 on KCNQ2/3 heterotetramer channel (the main mediate channel for in vivo M current) was 20 times or more and 30 times or more of that K21 ($EC_{50}$=990 nM) and RTG (it is reported that $EC_{50}$=1.6 μM, Sanker R, et al., *Epilepsia*, 2012, 53, 412-424), respectively, and the agonistic activity of K43 on KCNQ2/3 heterotetramer channel was also much higher than those of K21 and RTG.

III. Examples for Evaluation on Pharmacodynamical Effects of Compounds In Vivo

In Vivo Pharmacodynamical Effects Example 1:
Preventive and Therapeutic Effects of Compounds K41.HCl and K43.HCl Administered by Oral Perfusion on Animal Model Induced by MES (Maximum Electroshock)

YLS-9A model physiological pharmaceutical electronic stimulator was used in the experiment to induce convulsion of mice, and specific parameters were set as follows: configuration 8, stimulating voltage: 160V, period of stimulation: 5.4 sec. Healthy KM mice (SPF level, male, body weight: 18 to 22 g) were selected for the experiment. After the ear tip of the mice was sufficiently wetted with physiological saline, the mice was electrically stimulated once with ear clip electrode, and tonic hind-limb seizure was deemed as indication of convulsion. The mice were screened one day before the experiment to weed out the dead mice and the ones without generalized tonic seizure. The qualified mice were caged randomly with access to water at liberty. Before the experiment started, the mice were fasted for 8 h.

Figure 3:
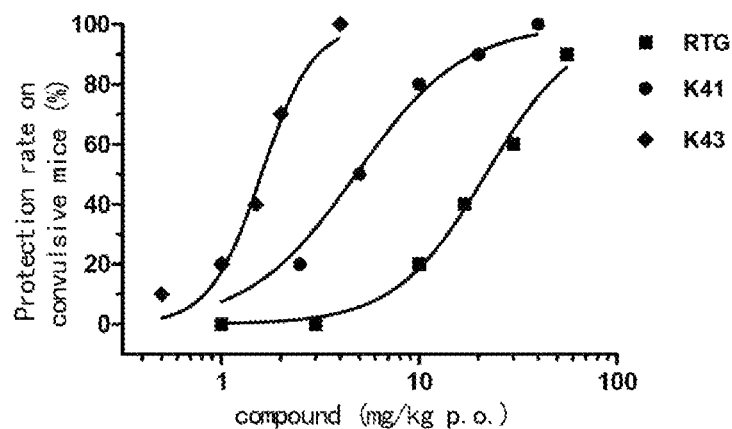
FIG. 3 is a graph showing the dose-response curves of K43 and K41 according to present invention and RTG against MES in vivo in mice.

The compounds to be tested were freshly formulated on the day of experiment. RTG hydrochloride was dissolved with ultrapure water to obtain a solution with desired concentration. K41.HCl and K43.HCl were formulated with 5% DMSO+95% of 1% Tween80, that is, a proper amount of the compound to be tested was weighted and, first, sufficiently dissolved in 5% DMSO, and then added with a desire volume of 1% Tween80 to be sufficiently suspended to form a suspension with a certain drug concentration. The mice screened one day before were randomly grouped with each group having 10 mice, marked, weighted and then administered with the compound to be tested or solvent (5% DMSO+95% (1% Tween 80)) by oral perfusion with administered volume of 0.2 ml/10 g. The dose range for each compound was 1 to 56 mg/kg for RTG, 1 to 40 mg/kg for K41.HCl, and 0.5 to 4 mg/kg for K43.HCl. 30 mins after administration, MES experiment was performed and the experimental parameters were the same as the above. The number of mice with generalized tonic-clonic convulsion in each group was recorded, the protection rate of each of the compounds to be tested on convulsive mice induce by MES was calculated and dose-response curve for each compound was plotted. The dose-response curve for each compound was obtained according to the analysis of Graphpad Prism 5 software, as shown in FIG. 3.

Results and discussion: the MES experimental results showed that each of the orally administered RTG hydrochloride, K41.HCl and K43.HCl shows a dose dependent protective effect on convulsive mice induce by MES. $ED_{50}$ (50% effective dose) of each of the compound was 21.80 mg/kg for RTG hydrochloride with a 95% CI (95% confidence interval) of; 19.03 to 24.97 mg/kg; 4.80 mg/kg for K41.HCl with a 95% CI of 3.42 to 6.74 mg/kg; and 1.60 mg/kg for K43.HCl with a 95% CI of 1.35 to 1.88 mg/kg. The efficacies of K43 and K31 against MES were higher than that of RTG.

IV. Examples for Evaluating $TD_{50}$ of Compound

Rotarod Experimental Example 1: Influence of K41.HCl and K43.HCl Administered by Oral Perfusion on Motor Coordination Ability of Mice YLS-4C Rotarod system was used in the experiment, wherein the diameter of the rod was 3 cm and the rotate speed was set at 6 rpm. Healthy KM mice (SPF level) were selected, wherein male and female were equal, the body weight was 18 to 22 g. One day before experiment, the mice were place on the rotarod for training and screening. The tail tip of mice was held to make them creep on the rotarod during the training. After creeping for a while, the tail tip of mice was gradually relaxed, and completely released when they did not rely on the tail to balance their body. The mice that jumped on the rotarod or griped the rotarod were weed out. In addition, three time periods were set with 1 min for each. The mice that did not fall off in all of the three time periods were qualified for testing. The qualified mice were randomly caged according to the gender, and allowed to eat and drink freely.

Figure 4:
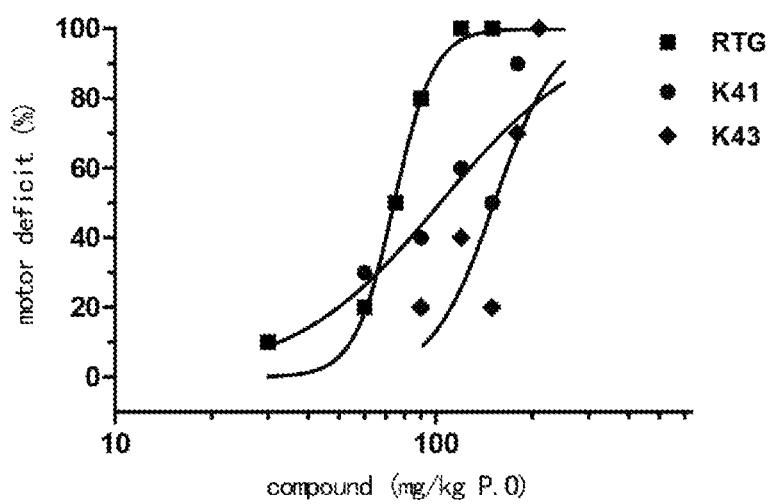
FIG. 4 is a graph showing the dose-response curves of K43 and K41 according to present invention and RTG on the athletic capability of mice.

On the day of the experiment, each compound to be tested was freshly formulated by the same method as described in MES experiment. If the compound was not sufficiently suspended, the suspension was further mixed by ultrasonication for 20 min so as to make the compound sufficiently suspended. The qualified mice screened one day before were randomly grouped with each group having 10 mice, marked, weighted and then administered with the compound to be tested or solvent (5% DMSO+95% (1% Tween 80)) by oral perfusion with a administered volume of 0.2 ml/kg. The dose range for each compound was 30 to 150 mg/kg for RTG, 30 to 180 mg/kg for K41.HCl, and 90 to 210 mg/kg for K43.HCl. 30 mins after administration, Rotarod experiment was performed and the experiment parameters were the same as the above. The number of mice that fell off from the rorarod was recorded, and the influence of each compound on motor coordination ability of mice was analyzed. The curve for dose of each compound verse motor deficit (percentage) of mice for each compound was obtained according to the analysis of Graphpad Prism 5 software and was shown in FIG. 4.

Results and discussion: $TD_{50}$ (50% acute neurotoxicity dose) of each compound obtained from the Rotarod experiment was 74.21 mg/kg for RTG with a 95% CI of 69.65 to 79.07 mg/kg; 103.40 mg/kg for K41.HCl with a 95% CI of 72.62 to 147.20 mg/kg; and 152.40 mg/kg for K43.HCl with a 95% CI of 104.30 to 222.60 mg/kg. P.I values of RTG, K41.HCl and K43.HCl in MES experiment, which were calculated according to the following equation: P.I (Protective index)=$TD_{50}/ED_{50}$, were 3.40, 21.54 and 95.25, respectively, indicating that K43 and K41 has a weaker neurotoxicity than RTG, thus possess a wider safety window.

V. Pharmacokinetical Examples

Pharmacokinetical Example 1, Research on Distribution of the Compounds K41.HCl and K43.HCl in Mice's Brain Tissue Formulation of the compound: K41.HCl was formulated to a 0.5 mg/ml solution for intragastric perfusion by using 16% DMSO/20% Tween 80/64% physiological saline; to a 0.2 mg/ml solution for intravenous injection by diluting the above solution for intragastric perfusion with physical saline containing 1% Tween 80. K43.HCl was formulated to a 0.5 mg/ml solution for intragastric perfusion by using 5% DMSO/5% Tween80/80% physiological saline; to a 0.2 mg/ml solution for intravenous injection by diluting the above solution for intragastric perfusion with physical saline containing 1% Tween 80.

Experimental Design 84 healthy ICR mice (male, body weight, 18-20 g) were fasted for 8 h with access to water at liberty before the experiment. The mice were fed at the same time 2 h after administration of the compound. Specific arrangement was shown in the following table.

| Group | Number of animals | Compound | Administration manner | Administration dose (mg/kg) | Administration volume (ml/kg) | Sampling time(h) |
|---|---|---|---|---|---|---|
| 1 | 27 | K41•HCl | Intragastric perfusion | 5 | 10 | 0.25, 0.5, 1, 2, 3, 4, 6, 8 and 24 h |

-continued

| Group | Number of animals | Compound | Administration manner | Administration dose (mg/kg) | Administration volume (ml/kg) | Sampling time(h) |
|---|---|---|---|---|---|---|
| 2 | 15 | K41•HCl | intravenous injection | 2 | 10 | 5 min, 0.25, 0.5, 1, 2, 4, 6, 8 and 24 h |
| 3 | 27 | K43•HCl | Intragastric perfusion | 5 | 10 | 0.25, 0.5, 1, 2, 3, 4, 6, 8 and 24 h |
| 4 | 15 | K43•HCl | Intravenous injection | 2 | 10 | 5 min, 0.25, 0.5, 1, 2, 4, 6, 8 and 24 h |

Sample Collection

After administration by intragastric perfusion, mice were sacrificed by cutting abdominal aorta at the time points set as the above with 3 mice for each time point. 0.5 mL of whole blood was collected for each animal, placed into a heparinized test tube and subjected to centrifugation at 11000 rpm for 5 min to separate plasma, which was then cryopreserved in a −20° C. refrigerator. After the animal was sacrificed, its whole brain was collected, washed with ice-cooled physiological saline to remove residual blood, absorbed to dryness, labeled and cryopreserved in a −20° C. refrigerator. After administration by intravenous injection, 0.5 mL of venous blood was collected from venous plexus behind eyeball, placed into a heparinized test tube and subjected to centrifugation at 11000 rpm for 5 min to separate plasma, which was then cryopreserved in a −20° C. refrigerator. The concentration of each compound in plasma and brain tissue was determined by LC-MS/MS.

Experimental Results

Pharmacokinetic parameters after administration were calculated according to the obtained data of plasma concentration, using the non-compartmental model of Phoenix 1.3 software (Pharsight Co., USA).

Pharmacokinetic parameters after administrating K41.HCl by intragastric perfusion at 5 mg/kg and intravenous injection at 2 mg/kg

| Parameters | Unit | Intragastric perfusion 5 mg/kg | | Intravenous injection 2 mg/kg |
|---|---|---|---|---|
| | | Plasma | Brain | Plasma |
| $T_{1/2}$ | (h) | 0.64 | 0.63 | 0.49 |
| $T_{max}$ | (h) | 0.25 | 0.25 | / |
| $C_{max}$ | (ng/ml or ng/g) | 606 | 1467 | / |
| $AUC_{0-t}$ | (ng · h/ml or ng · h/g) | 646 | 1680 | 281 |
| $AUC_{0-\infty}$ | (ng · h/ml or ng · h/g) | 654 | 1684 | 294 |
| $MRT_{0-\infty}$ | (h) | 1.04 | 1.10 | 0.45 |
| CL | (L/h/kg) | / | / | 6.81 |
| Vss | (L/kg) | / | / | 3.04 |
| F | (%) | 91.9 | / | / |
| $AUC_{0-t}$ ratio (brain/plasma) | | | 2.6 | |

Pharmacokinetic parameters after administrating K43.HCl by intragastric perfusion at 5 mg/kg and intravenous injection at 2 mg/kg

| Parameters | Unit | Intragastric perfusion 5 mg/kg | | intravenous injection 2 mg/kg |
|---|---|---|---|---|
| | | Plasma | Brain | Plasma |
| $T_{1/2}$ | (h) | 0.62 | 1.06 | 0.40 |
| $T_{max}$ | (h) | 0.25 | 0.25 | / |
| $C_{max}$ | (ng/ml or ng/g) | 350 | 1429 | / |
| $AUC_{0-t}$ | (ng · h/ml or ng · h/g) | 184 | 1329 | 326 |
| $AUC_{0-\infty}$ | (ng · h/ml or ng · h/g) | 189 | 1346 | 334 |
| $MRT_{0-\infty}$ | (h) | 0.94 | 1.29 | 0.43 |
| CL | (L/h/kg) | / | / | 6.00 |
| Vss | (L/kg) | / | / | 2.61 |
| F | (%) | 22.5 | / | / |
| $AUC_{0-t}$ ratio (brain/plasma) | | | 7.2 | |

Experimental Conclusion

After mice were administered with K41.HCl by intragastric perfusion at 5 mg/kg, the time for achieving the maximum concentrations ($T_{max}$) of K41.HCl in plasma and brain tissue was 0.25 h; the concentration of K41.HCl in brain tissue was 2.6 time of that in plasma. Oral bioavailability of K41.HCl in ICR mice was 91.9%.

After mice were administered with K43.HCl by intragastric perfusion at 5 mg/kg, the time for achieving the maximum concentrations ($T_{max}$) of K43.HCl in plasma and brain tissue was 0.25 h; the concentration of K43.HCl in brain tissue was 7.2 time of that in plasma. Oral bioavailability of K43.HCl in ICR mice was 22.5%.

It is reported in WO2013060097 that, under the same experimental conditions, the exposure amount of RTG in mice's brain was only 16% of that in plasma when RTG was administered by intragastric perfusion at 20 mg/kg, and the exposure amount of RTG was only 14% of that in plasma when RTG was administered by intravenous injection at 20 mg/kg. Thus, from the results of the in vivo pharmacokinetic experiment in mice, it can be seen that K41.HCl and K43.HCl have a better concentration distribution in brain tissue than RTG, and possess an equal or even higher distribution coefficient than K21 disclosed in WO2013060097 in brain tissue of mice.

Pharmacokinetical Example 2: Research on Distribution of K43 in Rats' Brain Tissue after Administration Via Intravenous Injection Experimental Purpose:

After K43 was administered to Sprague Dawley rats via intravenous injection or oral administration, blood sample and brain tissue were collected at different time points. the concentration of K43 in plasma and brain of rats after administration of the compounds was analyzed by LC-MS/MS and used to calculate the pharmacokinetic parameters, evaluating the oral bioavailability and distribution in brain tissue of K43 in rats.

Experimental Design

24 SD rats, which were provided by SHANGHAI SLAC LABORATORY ANIMAL CO. LTD., were used to perform the experiments according to the following table.

| | | | Administration information | | | | |
|---|---|---|---|---|---|---|---|
| Group | Number of animals Male | Compound | Administration dose (mg/kg) | Administration concentration* (mg/mL) | Administration volume (mL/kg) | Sampling manner | Administration manner |
| 1 | 3 | K43 | 0.500 | 0.500 | 1.00 | Plasma | IV |
| 2** | 3 | K43 | 5.00 | 0.500 | 10.0 | Plasma | PO |
| 3** | 3 | K43 | 5.00 | 0.500 | 10.0 | Brain | PO |
| 4** | 3 | K43 | 5.00 | 0.500 | 10.0 | Brain | PO |
| 5** | 3 | K43 | 5.00 | 0.500 | 10.0 | Brain | PO |
| 6** | 3 | K43 | 5.00 | 0.500 | 10.0 | Brain | PO |
| 7** | 3 | K43 | 5.00 | 0.500 | 10.0 | Brain | PO |
| 8** | 3 | K43 | 5.00 | 0.500 | 10.0 | Brain | PO |

*The concentration of the compound was calculated according to the free radicals.
**The second group was for collecting brain tissue at 24 h; the third group to the eighth group were for collecting brain tissue at the time point of 0.25, 0.5, 1, 2,4, 6 hr, respectively.

Sample Collection:

About 0.15 mL of blood was collected through orbit per animal every time, and EDTAK2 was used for anticoagulation. For IV group, the time points for collection were before administration (0 hr), and 5 min, 15 min, 30 min, 1 h, 2 h, 4 h, 6 h, 8 h and 24 h after administration; and for PO group, the time points for collection were before administration (0 hr), 15 min, 30 min, 1 h, 2 h, 4 h, 6 h, 8 h and 24 h after administration. The time points for collecting brain tissue were 0.25, 0.5, 1, 2, 4, 6 and 24 h. The collected blood samples were placed on icen, and plasma was centrifuged within 1 h (centrifugal condition: 12000 rpm, 2 min, 4° C.). The collected plasma was cryopreserved in a −20° C. refrigerator before analysis.

Experimental Results:

Pharmacokinetic parameters after administration were calculated according to the obtained data of plasma concentration using the non-compartmental model of WinNonlin V6.3.

Main pharmacokinetic parameters after intravenously administrating K43 (intravenous injection (IV), 0.500 mg/kg) to SD rats

| PK parameters | | IV-1 | IV-2 | IV-3 | Mean | SD | RSD (%) |
|---|---|---|---|---|---|---|---|
| Dose | $mg \cdot kg^{-1}$ | | | | 0.500 | | |
| $K_{el}$ | $h^{-1}$ | 0.552 | 0.427 | 0.516 | 0.498 | 0.641 | 13 |
| $t_{1/2}$ | h | 1.26 | 1.62 | 1.34 | 1.41 | 0.191 | 14 |
| $AUC_{0-t}$ | $h \cdot ng \cdot mL^{-1}$ | 219 | 232 | 239 | 230 | 10.4 | 4.5 |
| $AUC_{0-inf}$ | $h \cdot ng \cdot mL^{-1}$ | 221 | 236 | 242 | 233 | 10.9 | 4.7 |
| $AUMC_{0-t}$ | $h \cdot h \cdot ng \cdot mL^{-1}$ | 287 | 258 | 270 | 271 | 14.6 | 5.4 |
| $AUMC_{0-inf}$ | $h \cdot h \cdot ng \cdot mL^{-1}$ | 304 | 295 | 293 | 297 | 6.17 | 2.1 |
| CL | $mL \cdot kg^{-1} \cdot min^{-1}$ | 37.8 | 35.3 | 34.5 | 35.8 | 1.70 | 4.8 |
| $MRT_{IV}$ | h | 1.38 | 1.25 | 1.21 | 1.28 | 0.0879 | 6.9 |
| $Vd_{SS}$ | $L \cdot kg^{-1}$ | 3.13 | 2.65 | 2.51 | 2.76 | 0.324 | 12 |

Main pharmacokinetic parameters after administrating K43 (oral administration, PO, 5.00 mg/kg) to SD rats

| PK parameters | | PO-4 | PO-5 | PO-6 | Mean | SD | RSD (%) |
|---|---|---|---|---|---|---|---|
| Dose | $mg \cdot kg^{-1}$ | | | | 5.00 | | |
| $K_{el}$ | $h^{-1}$ | 0.186 | 0.0857 | 0.371 | 0.214 | 0.145 | 68 |
| $t_{1/2}$ | h | 3.74 | 8.09 | 1.87 | 4.56 | 3.19 | 70 |
| $t_{max}$ | h | 2.00 | 4.00 | 1.00 | 2.33 | 1.53 | 65 |
| $C_{max}$ | $ng \cdot mL^{-1}$ | 62.7 | 138 | 107 | 103 | 37.8 | 37 |
| $AUC_{0-t}$ | $h \cdot ng \cdot mL^{-1}$ | 467 | 1379 | 379 | 742 | 554 | 75 |
| $AUC_{0-inf}$ | $h \cdot ng \cdot mL^{-1}$ | 471 | 1605 | 407 | 828 | 674 | 81 |
| $AUMC_{0-t}$ | $h \cdot h \cdot ng \cdot mL^{-1}$ | 2360 | 10030 | 957 | 4449 | 4884 | 110 |
| $AUMC_{0-inf}$ | $h \cdot h \cdot ng \cdot mL^{-1}$ | 2497 | 18103 | 1256 | 7285 | 9389 | 129 |
| $MRT_{PO}$ | h | 5.30 | 11.3 | 3.09 | 6.55 | 4.236 | 65 |
| F | % | 20.3 | 59.9 | 16.5 | 32.2 | 24.1 | 75 |

Main pharmacokinetic parameters in brain tissue after administrating K43 (oral administration, PO, 5.00 mg/kg) to SD rats.

| PK parameters | | |
|---|---|---|
| Dose | mg·kg$^{-1}$ | 5.00 |
| $K_{el}$ | h$^{-1}$ | 0.0542 |
| $t_{1/2}$ | h | 12.8 |
| $t_{max}$ | h | 2.00 |
| $C_{max}$ | ng·g$^{-1}$ | 366 |
| AUC$_{0-t}$ | h·ng·g$^{-1}$ | 2895 |
| AUC$_{0-inf}$ | h·ng·g$^{-1}$ | 4314 |
| AUMC$_{0-t}$ | h·h·ng·g$^{-1}$ | 25306 |
| AUMC$_{0-inf}$ | h·h·ng·g$^{-1}$ | 85535 |
| MRT$_{PO}$ | h | 19.8 |

Experimental Results:

The results of research on pharmacokinetics and distribution in brain tissue of K43 in rats showed that the half life in rats after intravenous injection (IV) (dose: 0.5 mg/kg) was 1.41±0.191 hr, clearance (CL) was 35.8±1.70 mL/kg/min, and Vss was 2.76±0.324 L/kg.

The average time for achieving the maximum plasma concentration in rats after oral administration (PO) K43 (dose: 5.00 mg/kg) was 2.33±1.53 hr, the maximum plasma concentration was 103±37.8 ng/mL, AUC$_{0\to24\ hr}$ was 742±554 hr*ng/mL, and the oral bioavailability of K43 in SD rats was 32.2±24.1%.

The average time for achieving the maximum concentration in brain tissue of rats after oral administration (PO) K43 (dose: 5.00 mg/kg) was 2.00 hr, the average maximum concentration was 366 ng/g, AUC$_{0\to24\ hr}$ was 2895 hr*ng/g, AUC$_{0\to24\ hr}$ of K43 in brain tissue of SD rats is 3.9 times of that in plasma.

What is claimed is:

1. A method for treating a neurological disease selected from the group consisting of epilepsy, convulsion, neuropathic pain, acute ischemic stroke, and Alzheimer's disease, comprising:
   administering to a subject in need thereof an effective amount of a compound represented by formula I or a pharmaceutical acceptable salt thereof,

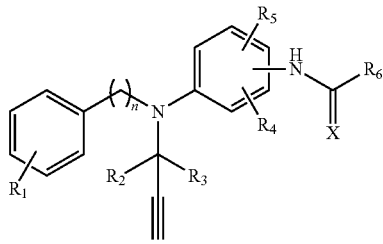

I wherein,

X is selected from a group consisting of oxygen and sulfur;

n is 1, 2 or 3;

$R_1$ is H or halogen;

$R_2$ and $R_3$ are each independently selected from a group consisting of H, D and $C_1$-$C_3$ alkyl; or $R_2$ and $R_3$ together with the carbon atom to which they attached form $C_3$-$C_6$ saturated ring;

$R_4$ and $R_5$ are each independently selected from a group consisting of H; halogen; $C_1$-$C_6$ alkyl; $C_3$-$C_6$ cycloalkyl; cyano; alkoxyl; $C_1$-$C_6$ alkyl substituted by hydroxy, amino, $C_1$-$C_4$ alkoxy, $C_1$-$C_4$ alkylcarbonyl, or halogen; $C_1$-$C_4$ alkoxy substituted by halogen; $C_1$-$C_6$ alkylcarbonyl; $C_1$-$C_6$ alkoxycarbonyl; $C_1$-$C_6$ alkylaminocarbonyl; $C_2$-$C_6$ alkenyl; and $C_2$-$C_6$ alkynyl; provided that $R_4$ and $R_5$ are not simultaneously hydrogen;

$R_6$ is selected from a group consisting of $C_1$-$C_6$ alkoxy; $C_1$-$C_6$ alkylamino; $C_1$-$C_6$ alkyl; $C_3$-$C_6$ cycloalkyl; $C_2$-$C_6$ alkenyl; $C_2$-$C_6$ alkynyl; $C_6$-$C_{10}$ aryl; $C_1$-$C_6$ alkyl substituted by halogen, cyano, hydroxy, $C_1$-$C_6$ alkoxyl, di($C_1$-$C_4$ alkyl) amino, $C_1$-$C_6$ alkylcarbonyl, $C_1$-$C_6$ alkylcarbonylamino, or $C_1$-$C_6$ alkoxycarbonyl; $C_3$-$C_6$ cycloalkyl substituted by halogen; $C_2$-$C_6$ alkenyl substituted by halogen; $C_2$-$C_6$ alkynyl substituted by halogen; tetrahydrofuranyl; and

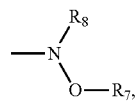

wherein, $R_7$ and $R_8$ are each independently selected from a group consisting of $C_1$-$C_4$ alkyl.

2. The method according to claim 1, wherein, $R_1$ is H or fluorine;

$R_2$ and $R_3$ are each independently selected from a group consisting of H and D, or $R_2$ and $R_3$ together with the carbon atom to which they attached form cyclopropyl;

one of $R_4$ and $R_5$ is $C_1$-$C_4$ alkyl, and the other is H or $C_1$-$C_4$ alkyl.

3. The method according to claim 1, wherein the compound is represented by formula II:

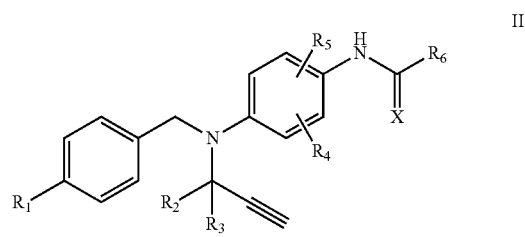

II wherein,

X is selected from a group consisting of oxygen and sulfur;

$R_1$ is H or halogen;

$R_2$ and $R_3$ are each independently selected from a group consisting of H, D and $C_1$-$C_3$ alkyl; or $R_2$ and $R_3$ together with the carbon atom to which they attached form $C_3$-$C_6$ saturated ring;

$R_4$ and $R_5$ are each independently selected from a group consisting of H; halogen; $C_1$-$C_6$ alkyl; $C_3$-$C_6$ cycloalkyl; cyano; $C_1$-$C_4$ alkoxyl; $C_1$-$C_6$ alkyl substituted by hydroxy, amino, $C_1$-$C_4$ alkoxy, $C_1$-$C_4$ alkylcarbonyl, or halogen; $C_1$-$C_4$ alkoxy substituted by halogen; $C_1$-$C_6$ alkylcarbonyl; $C_1$-$C_6$ alkoxycarbonyl; $C_1$-$C_6$ alkylaminocarbonyl; $C_2$-$C_6$ alkenyl; and $C_2$-$C_6$ alkynyl; provided that $R_4$ and $R_5$ are not simultaneously hydrogen;

$R_6$ is selected from a group consisting of $C_1$-$C_6$ alkoxy; $C_1$-$C_6$ alkylamino; $C_1$-$C_6$ alkyl; $C_3$-$C_6$ cycloalkyl; $C_2$-$C_6$ alkenyl; $C_2$-$C_6$ alkynyl; $C_6$-$C_{10}$ aryl; $C_1$-$C_6$ alkyl substituted by halogen, cyano, hydroxy, $C_1$-$C_6$ alkoxyl, di($C_1$-$C_4$ alkyl) amino, $C_1$-$C_6$ alkylcarbonyl, $C_1$-$C_6$ alkylcarbonylamino, or $C_1$-$C_6$ alkoxycarbonyl; $C_3$-$C_6$ cycloalkyl substituted by halogen; $C_2$-$C_6$ alkenyl substituted by halogen; C$_2$-C$_6$ alkynyl substituted by halogen; tetrahydrofuranyl; and

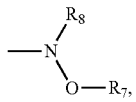

wherein, R$_7$ and R$_8$ are each independently selected from a group consisting of C$_1$-C$_4$ alkyl.

4. The method according to claim 3, wherein,
R$_1$ is H or fluorine;
R$_2$ and R$_3$ are each independently selected from a group consisting of H and D, or R$_2$ and R$_3$ together with the carbon atom to which they attached form cyclopropyl;
one of R$_4$ and R$_5$ is C$_1$-C$_4$ alkyl, and the other is H or C$_1$-C$_4$ alkyl.

5. The method according to claim 1, wherein the compound has a structure selected from the following formula III to V:

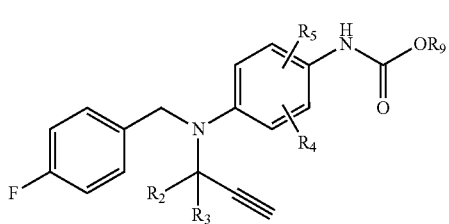

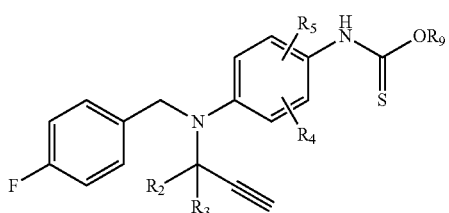

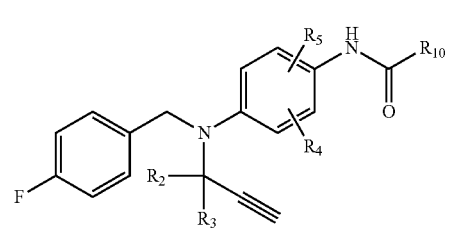

wherein,
R$_2$ and R$_3$ are each independently selected from a group consisting of H, D and C$_1$-C$_3$ alkyl; or R$_2$ and R$_3$ together with the carbon atom to which they attached form C$_3$-C$_6$ saturated ring;
R$_4$ and R$_5$ are each independently selected from a group consisting of H; C$_1$-C$_6$ alkyl; C$_1$-C$_4$ alkoxyl; C$_1$-C$_6$ alkyl substituted by halogen; C$_1$-C$_4$ alkoxy substituted by halogen; provided that R$_4$ and R$_5$ are not simultaneously hydrogen;
R$_9$ is selected from a group consisting of C$_1$-C$_6$ alkyl and C$_3$-C$_6$ cycloalkyl;
R$_{10}$ is selected from a group consisting of C$_1$-C$_6$ alkyl; C$_1$-C$_6$ alkyl substituted by halogen, cyano, hydroxy, C$_1$-C$_6$ alkoxyl, di(C$_1$-C$_4$ alkyl)amino, C$_1$-C$_6$ alkylcarbonyl, C$_1$-C$_6$ alkylamido, or C$_1$-C$_6$ alkoxycarbonyl;

C$_3$-C$_6$ cycloalkyl; and C$_3$-C$_6$ cycloalkyl substituted by halogen; tetrahydrofuranyl; and

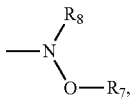

wherein, R$_7$ and R$_8$ are each indepently selected from a group consisting of C$_1$-C$_4$ alkyl.

6. The method according to claim 5, wherein,
R$_2$ and R$_3$ are each independently selected from a group consisting of H and D, or R$_2$ and R$_3$ together with the carbon atom to which they attached form cyclopropyl;
one of R$_4$ and R$_5$ is C$_1$-C$_1$ alkyl, and the other is H or C$_1$-C$_4$ alkyl;
R$_9$ is selected from a group consisting of C$_1$-C$_6$ alkyl and C$_3$-C$_6$ cycloalkyl;
R$_{10}$ is selected from a group consisting of C$_1$-C$_6$ alkyl; C$_1$-C$_6$ alkyl substituted by halogen, cyano, hydroxy, C$_1$-C$_6$ alkoxyl, di(C$_1$-C$_4$ alkyl)amino, C$_1$-C$_6$ alkylcarbonyl, C$_1$-C$_6$ alkylamido, or C$_1$-C$_6$ alkoxycarbonyl;
C$_3$-C$_6$ cycloalkyl; C$_3$-C$_6$ cycloalkyl substituted by halogen; tetrahydrofuranyl; and

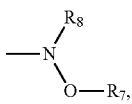

wherein, R$_7$ and R$_8$ are each indepently selected from a group consisting of C$_1$-C$_4$ alkyl.

7. The method according to claim 5, wherein,
R$_9$ is selected from a group consisting of methyl, ethyl and propyl;
R$_{10}$ is selected from a group consisting of C$_1$-C$_3$ alkyl; C$_1$-C$_3$ alkyl substituted by halogen, cyano, hydroxy, C$_1$-C$_3$ alkoxyl, di(C$_1$-C$_3$ alkyl)amino, C$_1$-C$_3$ alkylcarbonyl, C$_1$-C$_3$ alkylamido, or C$_1$-C$_3$ alkoxycarbonyl; C$_3$-C$_6$ cycloakyl; C$_3$-C$_6$ cycloakyl substituted by halogen; tetrahydrofuranyl; and

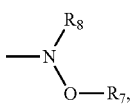

wherein, R$_7$ and R$_8$ are each independently selected from a group consisting of C$_1$-C$_3$ alkyl.

8. The method according to claim 1, wherein one of R$_4$ and R$_5$ is methyl, and the other is H or methyl.

9. The method according to claim 1, wherein the pharmaceutical acceptable salt is a salt formed by reacting the compound with an acid.

10. The method according to claim 9, wherein the acid is selected from a group consisting of maleic acid, succinic acid, citric acid, tartaric acid, fumaric acid, formic acid, acetic acid, propanoic acid, propandioic acid, oxalic acid, benzoic acid, phthalic acid, methanesulfonic acid, benzenesulfonic acid, toluenesulfonic acid, naphthalenesulfonic acid, 1,5-naphthalenedisulfonic acid, camphoric acid, camphor sulfonic acid, salicylic acid, acetyl salicylic acid, aspartic acid, glutamic acid, lactic acid, gluconic acid, ascorbic acid, gallic acid, amygdalic acid, malic acid, sorbic acid, trifluoroacetic acid, taurine, homotaurine, isethionic acid, cinnamic acid, hydrochloric acid, hydrobromic acid, hydroiodic acid, sulfuric acid, nitric acid, phosphoric acid and perchloric acid.

11. The method according to claim 1, wherein the compound represented by formula I or the pharmaceutical acceptable salt thereof is formulated into a pharmaceutical composition comprising the compound represented by formula I or the pharmaceutical acceptable salt thereof as an active ingredient and a pharmaceutical acceptable adjuvant.

12. The method according to claim 1, wherein the pharmaceutical composition is a KCNQ potassium channel agonist.

13. A method for treating a neurological disease selected from the group consisting of epilepsy, convulsion, neuropathic pain, acute ischemic stroke, and Alzheimer's disease, comprising:
administering to a subject in need thereof an effective amount of a compound selected from the group consisting of K40
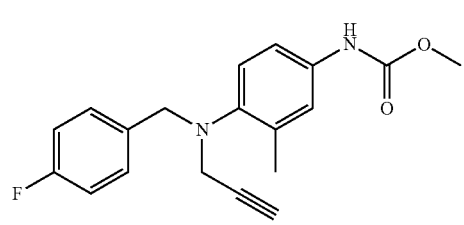

K41
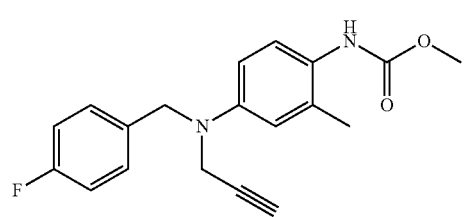

K42
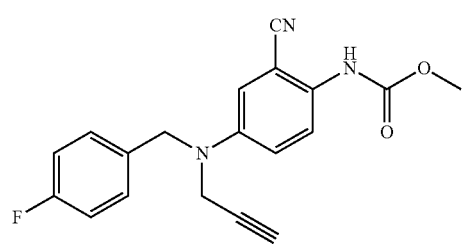

K43
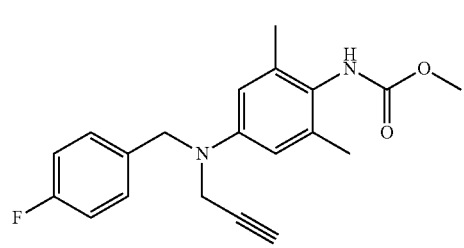

K44
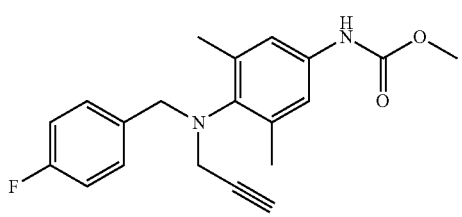

K45
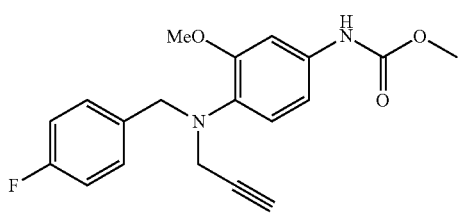

K46
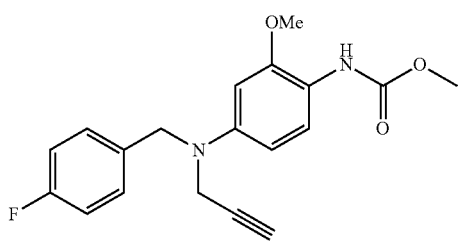

K47
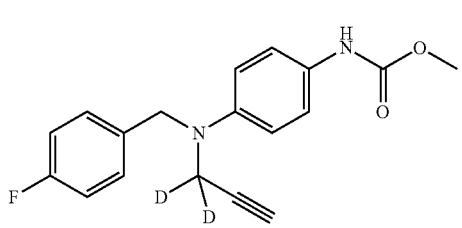

K48
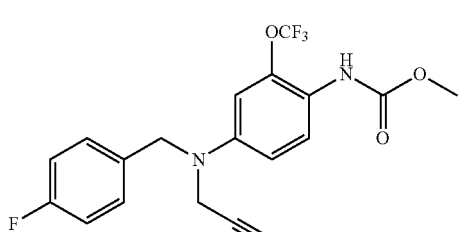

K49
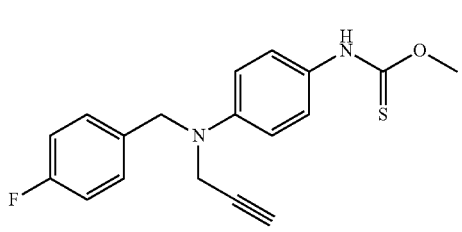

K50
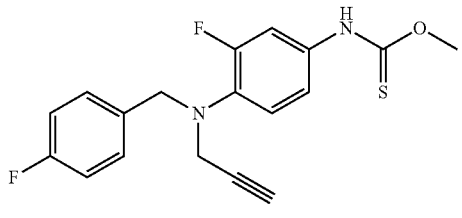

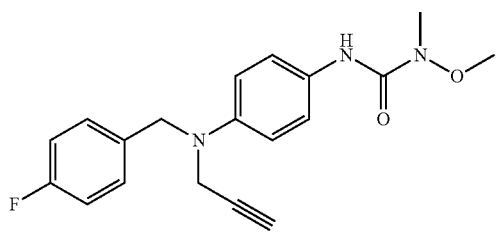

and pharmaceutical acceptable salts thereof.

14. The method according to claim 13, wherein the pharmaceutical acceptable salt is a salt formed by reacting the compound with an acid.

15. The method according to claim 14, wherein the acid is selected from a group consisting of maleic acid, succinic acid, citric acid, tartaric acid, fumaric acid, formic acid, acetic acid, propanoic acid, propandioic acid, oxalic acid, benzoic acid, phthalic acid, methanesulfonic acid, benzenesulfonic acid, toluenesulfonic acid, naphthalenesulfonic acid, 1,5-naphthalenedisulfonic acid, camphoric acid, camphor sulfonic acid, salicylic acid, acetyl salicylic acid, aspartic acid, glutamic acid, lactic acid, gluconic acid, ascorbic acid, gallic acid, amygdalic acid, malic acid, sorbic acid, trifluoroacetic acid, taurine, homotaurine, isethionic acid, cinnamic acid, hydrochloric acid, hydrobromic acid, hydroiodic acid, sulfuric acid, nitric acid, phosphoric acid and perchloric acid.

16. The method according to claim 13, wherein the compound or the pharmaceutical acceptable salt thereof is formulated into a pharmaceutical composition comprising the compound represented by formula I or the pharmaceutical acceptable salt thereof as an active ingredient and a pharmaceutical acceptable adjuvant.

17. The method according to claim 16, wherein the pharmaceutical composition is a KCNQ potassium channel agonist.

* * * * *